(12) United States Patent
Elson et al.

(10) Patent No.: US 7,449,306 B2
(45) Date of Patent: Nov. 11, 2008

(54) SYSTEMS AND METHODS FOR SCREENING PHARMACEUTICAL CHEMICALS

(75) Inventors: Elliot Elson, University City, MO (US); William B. McConnaughey, St. Louis, MO (US); Tetsuro Wakatsuki, University City, MO (US)

(73) Assignee: Washington University in St. Louis, St. Louis, MO (US)

(*) Notice: Subject to any disclaimer, the term of this patent is extended or adjusted under 35 U.S.C. 154(b) by 327 days.

(21) Appl. No.: 10/219,097

(22) Filed: Aug. 14, 2002

(65) Prior Publication Data
US 2003/0064358 A1 Apr. 3, 2003

Related U.S. Application Data

(60) Provisional application No. 60/312,322, filed on Aug. 14, 2001.

(51) Int. Cl.
G01N 33/48 (2006.01)
C12N 5/08 (2006.01)
C12N 5/02 (2006.01)

(52) U.S. Cl. .................. 435/40.52; 435/40.5; 435/325; 435/371

(58) Field of Classification Search ................ 435/40.5, 435/40.52, 371, 366, 325
See application file for complete search history.

(56) References Cited

U.S. PATENT DOCUMENTS

| | | | |
|---|---|---|---|
| 4,593,042 A | 6/1986 | Liang | |
| 4,705,785 A | 11/1987 | Schwedner et al. | |
| 5,038,795 A | 8/1991 | Roush et al. | |
| 5,326,357 A | 7/1994 | Kandel | |
| 5,464,853 A | 11/1995 | Chan et al. | |
| 5,571,083 A * | 11/1996 | Lemelson | 604/522 |
| 5,665,391 A | 9/1997 | Lea | |
| 5,706,815 A | 1/1998 | Sarvazyan et al. | |
| 6,332,364 B1 * | 12/2001 | Buschmann et al. | 73/788 |
| 2003/0091979 A1 | 5/2003 | Eschenhagen | |
| 2006/0105357 A1 * | 5/2006 | Benesch et al. | 435/6 |

FOREIGN PATENT DOCUMENTS

| | | |
|---|---|---|
| DE | 19500498 | 7/1996 |
| EP | 1 250 416 | 5/2006 |
| WO | 2001/00856 | 8/2001 |
| WO | WO 03/016860 | 2/2003 |

OTHER PUBLICATIONS

Paul et al. Effects of microtubules disruption on force, velocity, stiffness and [Ca2+]i in procine coronary arteries. Am. J. Physiol. Heart Circ. Physiol. (Nov. 2000) 279: H24-H2501.*
Wakatsuki et al. Cell Machanics studies by a reconstituted model tissue, Biophysical J. (Nov. 2000) 79: 2353-2368.*
Shen et al. Pharmacological modulation of the mechanical response of airway smooth muscle to length oscillation. J. Appl. Physiol. (1997) 83(3): 739-745.*
Kolodney et al. Isometric contration by fibroblasts and endothelial cells in tissue culture: A quantitative study. J. Cell Biol. (1992) 117(1): 73-82.*
Floyd et al. Ex vivo gene transfer using adenovirus-mediated full-length dystrophin delivery to dystrophic muscles. Gene Therapy (1997) 5: 19-30.*
Pasternak et al. Mechanical function of dystrophin in muscle cells. J. Cell Biol. (1995) 128(3): 355-361.*
DeWolf et al. Interaction of dystrophin fragments with model membranes. Biophys. J. (1997) 72(6): 2599-2604.*
Web site for Webster's Third International Dictionary, unabridged, www.lionreference.chadwyck.com, 6 pages; retrieved on Sep. 19, 2006.*
Allen, F.D. et al., "Calpain regulated cell adhesion in EGF-stimulated fibroblast-populated-collagen-lattice contraction," BED (American Society of Mechanical Engineers), 50 (Proceedings of the Bioengineering Conference, Jun. 27-Jul. 1, 2001), 353-354.
Eschenhagen, T. et al., " Transfection studies using a new cardiac 3D gel system," Molecular Approaches to Heart Failure Therapy, Hasenfuss et al. eds., Verlag Gmbh & Co., Germany (2000) 144-156.
Eschenhagen, T. et al., "Three-dimensional reconstitution of embryonic cardiomyocytes in a collagen matrix: a new heart muscle model system," FASEB J. (1997) 11(8):683-694.
Fink, C. et al., "Chronic stretch of engineered heart tissue induces hypertrophy and functional improvement," FASEB J. (2000) 14(5):669-679.
Kolodney, M.S. et al., "Correlation of myosin light chain phosphorylation with isometric contraction of fibroblasts," J. Biol. Chem. (1993) 268(32):23850-23855.
Petersen, N.W. et al., "Dependence of locally measured cellular derformability on position on the cell, temperature, and cytochalasin B," Proc. Natl. Acad. Sci. USA (1982) 79:5327-5331.
Sundberg, S.A., "High-throughput and ultra-high-throughput screening: solution- and cell-based approaches," Curr. Opin. Biotechnol. (2000) 11:47-53.
Wakatsuki, T. et al., "Phenotypic screening for pharmaceuticals using tissue constructs," Curr. Pharm. Biotech. (2004) 5(2):181-189.
Wakatsuki, T. et al, "Effects of cytochalasin D and latrunculin B on mechanical properties of cells," J. Cell Science (2001) 114(5):1025-1036.
Zahalak, G.I. et al., "Determination of cellular mechanical properties by cell poking, with an application to leukocytes," J. Biomech. Engin. (1990) 112:283-294.
Zimmerman, W.H. et al., "Three-dimensional engineered heart tissue from neonatal rat cardiac myocytes," Biotech. Bioeng. (2000) 68(1):106-114.

* cited by examiner

*Primary Examiner*—Irene Marx
*Assistant Examiner*—Susan Hanley
(74) *Attorney, Agent, or Firm*—Michael Best & Friedrich LLP

(57) ABSTRACT

A method for obtaining a response of a tissue model system to an activator includes contacting a bio-artificial tissue model system with an activator and measuring cellular mechanical response thereto of at least one of contractile force and tissue stiffness. A method for obtaining a response of a tissue model system to an activator includes contacting a bio-artificial tissue model system with an activator and measuring cellular mechanical response thereto of at least one of contractile force and hysteresis.

79 Claims, 24 Drawing Sheets

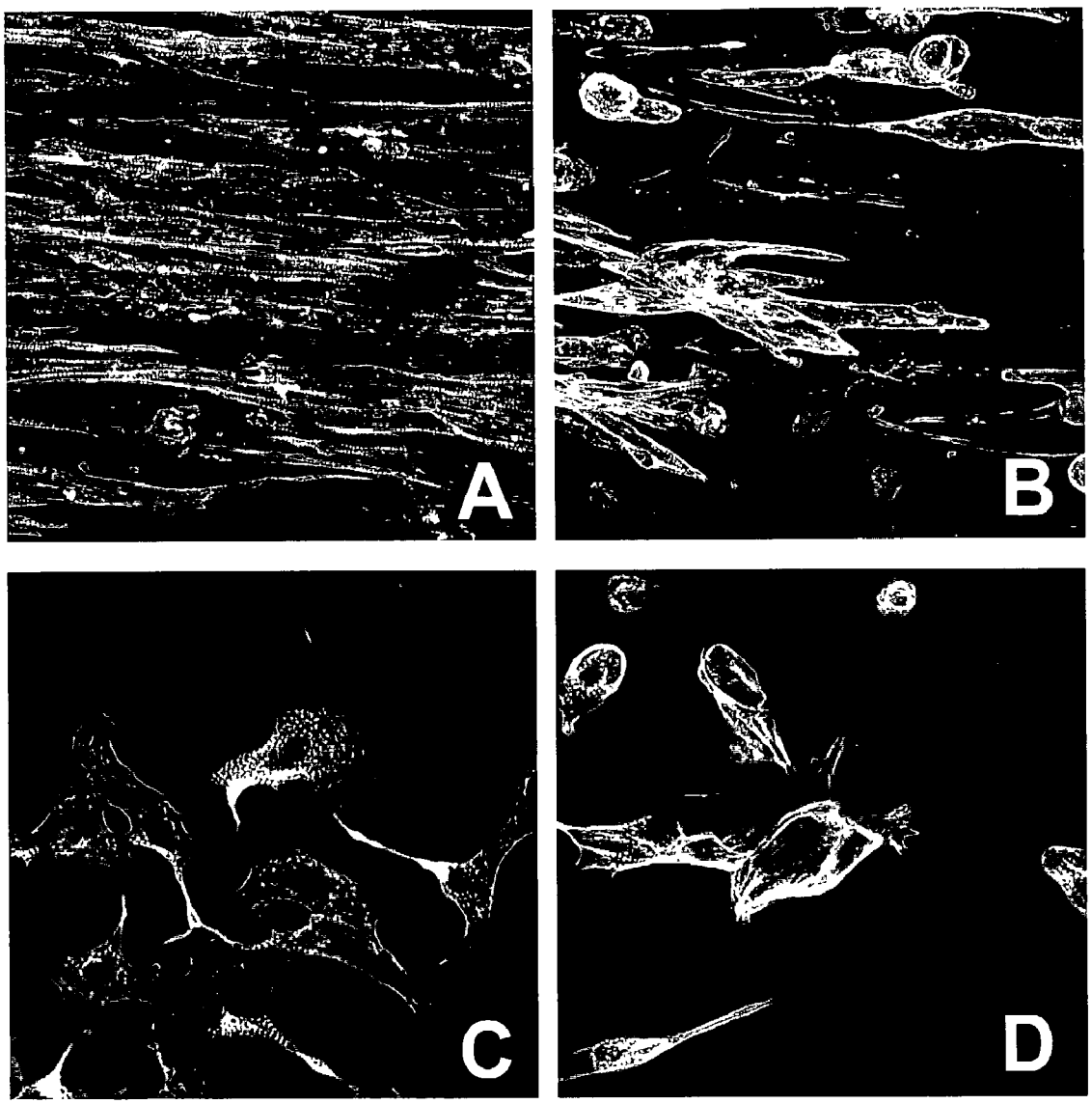

| Conditions | Contractility |
|---|---|
| DMEM supplemented with 10% FBS | No contraction |
| Cardiac Tissue Medium | Contraction after 7 to 8 days |
| Fibroblasts Conditioning Medium | Contraction after 4 to 5 days |
| Cocluture with Feeding Fibroblast Layer | Strong Contraction after 4 to 5 days |
| Coculture with Artificial Tissue with Fibroblasts | Strong Contraction after 4 to 5 days |
| Mixing Fibroblasts in the Tissue | Contraction after 4 to 5 days but reduction in contraction in 7 to 8 days |

Figure 5

SYSTEMS AND METHODS FOR SCREENING PHARMACEUTICAL CHEMICALS

CROSS-REFERENCE TO RELATED APPLICATIONS

This application claims the benefit of U.S. provisional patent application No. 60/312,322 filed Aug. 14, 2001, which is incorporated herein in its entirety by reference.

BACKGROUND OF THE INVENTION

This invention relates to systems and methods for screening pharmaceutical chemicals. More in particular, this invention relates to systems and methods for screening pharmaceutical chemicals in tissue models.

The number of pharmaceutical chemicals that must be tested for efficacy has increased enormously, mainly due to the development of large libraries of chemicals obtained using parallel and combinatorial chemical synthesis methods. Correspondingly, the number of identified therapeutic targets such as receptor and intracellular regulatory proteins has been greatly increased by the application of functional genomics. Therefore, there is a great need for rapid and quantitative methods with which to screen pharmaceutical chemical(s) for their ability to elicit specific cellular responses and to identify leading pharmaceutical candidates.

Initial screening of large libraries of chemicals is carried out by testing for specific binding to target molecules using assay methods that operate in solution. High throughput methods have been developed based on scintillation proximity assay or fluorescence detection techniques (Sundberg, 2000). These methods, while readily adapted to screen thousands of compounds per day, provide information only about the strength and specificity of chemical interaction, not about cell response. Hence, chemicals that are initially selected based on their ability to bind to a target in solution must be rescreened to assess their ability to elicit a desired cellular response. These secondary and tertiary levels of screening add increased expense and time to the process of detecting promising or lead pharmaceutical chemicals.

Stimulation of receptors and activation of ion channels have been assessed using fluorescence methods to detect changes in, e.g., calcium ion concentration and, membrane potential and pH (Sundberg, 2000). These changes in ion concentration and transport often occur relatively early in the process of signal transduction and lead to more specific end responses such as the activation of specific enzymes. Hence, measurement of these responses does not necessarily provide information about the ultimate cellular responses that are activated or inhibited by a test pharmaceutical compound.

BRIEF SUMMARY OF THE INVENTION

In one embodiment, a method is provided for obtaining a response of a multi-cell tissue model system to an agent which comprises contacting a tissue model with the agent and determining the cellular mechanical response to that contact of at least one of contractile force and tissue stiffness.

In another embodiment, a system is provided for obtaining a response of a tissue model system to an agent which comprises constructing a tissue model, providing an agent, and measuring cellular mechanical response to contact of the agent to the system of at least one of contractile force and hysteresis.

In a further embodiment, a system is provided for obtaining a mechanical response profile based on mechanical measurements of the response of reconstituted muscle and nonmuscle tissue models to an agent, which comprises constructing a tissue model system having cells reconstituted in collagen and contacting the reconstituted cells with an agent. The mechanical response comprises at least one of contractile force and tissue stiffness.

In a further embodiment, a method is provided for screening pharmaceuticals, which comprises contacting a tissue model comprising reconstituted cells in collagen with an effective amount of a pharmaceutical chemical and measuring cellular response to the chemical in terms of at least one of contractile force or tissue stiffness.

In a further embodiment, a method is provided for managing a library of one or more pharmaceuticals or pharmaceutical chemicals which comprises obtaining a profile of a mechanical response to the contact of an agent with a tissue model, storing that profile in a database, storing at least one additional profile of another pharmaceutical in the database, setting up a means for comparing more than one profile with another profile, comparing the profile of a first pharmaceutical with a profile of a second pharmaceutical based on a pre-established or ordered standard/hierarchy of comparison and ranking the pharmaceuticals in an order of activity with respect to mechanical effect on a tissue model.

In a further embodiment, a method is provided for obtaining a multi-parameter mechanical response profile for a tissue model contacted with a pharmaceutical measuring the cellular response thereof.

In a further embodiment, a tissue model is provided, the tissue model comprises tissue assembled in the form of a ring mounted on a system comprising an isometric force transducer electrically coupled to a computer. The tissue model spans the isometric force transducer and a computer-controlled stepping motor provides an application of stretching and strain to the tissue.

In a further embodiment, a tissue model is provided wherein said tissue model comprises a membrane of reconstituted tissue supported by a frame. The mechanical properties of the membrane of reconstituted tissue are determined from resistance to stretching as the tissue is moved against a probe attached to an isometric force transducer.

In a further embodiment, a method is provided for preparing a tissue model, said method comprises placing self assembling tissue in a shape on a support, and subjecting said shaped tissue to an application of stretch by application of indentation.

In a further embodiment, a method is provided for establishing a mechanical response profile of a pharmaceutical which comprises contacting or relaxing a tissue model with a pharmaceutical and determining the mechanical response(s) of the tissue model in terms of at least one of contractile force and stiffness.

In another aspect, a method of culturing a cardiac tissue is provided using a medium(s) conditioned by a fibroblast(s).

In another aspect, this invention comprises a method to identify the effect of a drug upon a tissue which comprises treating a tissue using this invention and measuring the effect so resulting, and thereafter comparing such measured effect with a standard drug effect on the same or similar tissue.

In another aspect, this invention comprises a method to data mine a library of pharmaceutical moieties for activity in tissue, which comprises treating a tissue using this invention and measuring the effect so resulting. Optionally, the measured effect may be compared with a correspondingly measured effect of a standard drug on the same or similar tissue.

In another aspect, this invention comprises a method of optimizing tissue culture conditions for constructing implantable artificial cardiac tissue, with additional different factors influencing cardiac tissue development including growth factors, and matrix proteins and hormones to a tissue model of the invention.

BRIEF DESCRIPTION OF THE DRAWINGS

FIG. 1 illustrates an exemplary method of preparation and measurement overall.

FIG. 3a shows the change in force and dynamic stiffness in response to activation by fetal bovine serum. FIG. 3b shows the change in force and dynamic stiffness resulting from disruption of the actin cytoskeleton by 2 μM cytochalasin D (CD) FIG. 3c is a summary of the data from both 3a and 3b to show the overall (linear) dependence of dynamic stiffness on force.

FIGS. 4a and 4b show contractile force and stiffness, respectively, generated by the tissue models after treatment with various concentrations of CD. FIGS. 4c and 4d show contractile force and stiffness, respectively, generated by the tissue models after treatment with various concentrations of LA-B.

FIG. 5 shows the degrees of cardiac myocytes spreading in various tissue culture conditions. FIG. 5a shows well spread cardiac myocytes in a cardiac tissue model made in a conditioned medium prepared with cardiac fibroblasts. Cardiac myocytes cultured in Dulbecco's modified Eagle's medium (DMEM) with 10% fetal bovine serum, shown in FIG. 5b, do not spread well. Cardiac myocytes cultured on tissue culture dishes with and without conditioned medium are shown in FIGS. 5c and 5d, respectively. The supplemental table in the FIG. 5 shows spontaneous contractility of cardiac tissue models made with various culture conditions.

FIG. 8a shows disassembled small and regular size molds schematically shown in FIG. 1e. FIG. 8b shows assembled small and regular size molds schematically shown in FIG. 1c. FIG. 8c shows photo images of small size tissue models made using small size mold held by a spacer. FIG. 8d shows photo image of regular size tissue models held by the spacer schematically shown in FIG. 6.

FIG. 12(b) shows a plot of force verses indentation depth for the same data as for FIG. 12(a) including also the effect of adding 40 nM CD and 2 μM CD.

As used herein, the term "agonist" includes a chemical substance that activates a cellular response.

Figure 15:
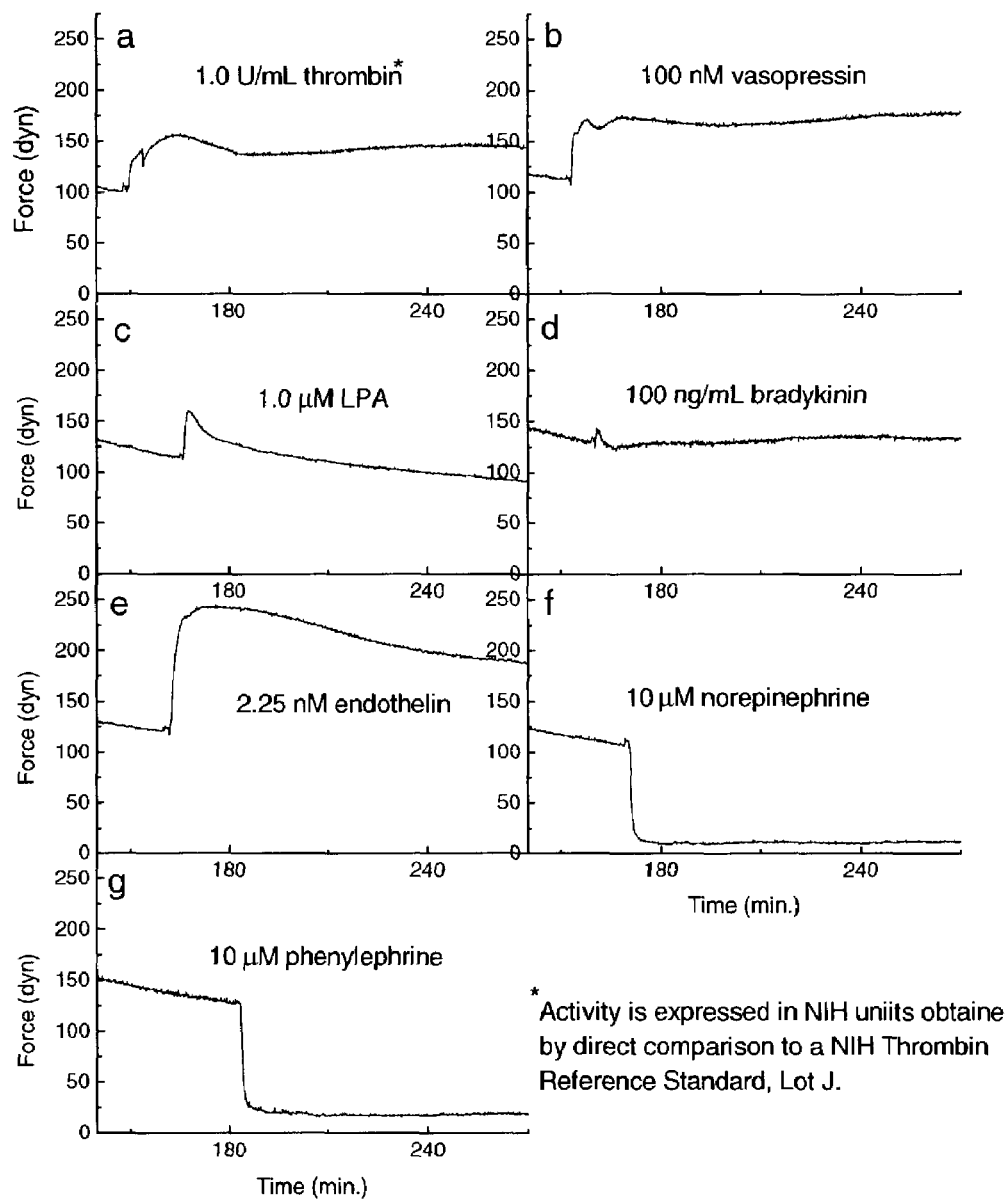

FIG. 15 shows the resulting forces (dynes) of a series of tests wherein several agonists are added to a tissue model of a ring system with smooth muscle cells. Panel a, b, c, d, e, f and g are profiles of force response by treatments of thrombin, vasopressin, LPA, bradykinin, endothelin, norepinephrine and phenylephrine, respectively.

Figure 16:
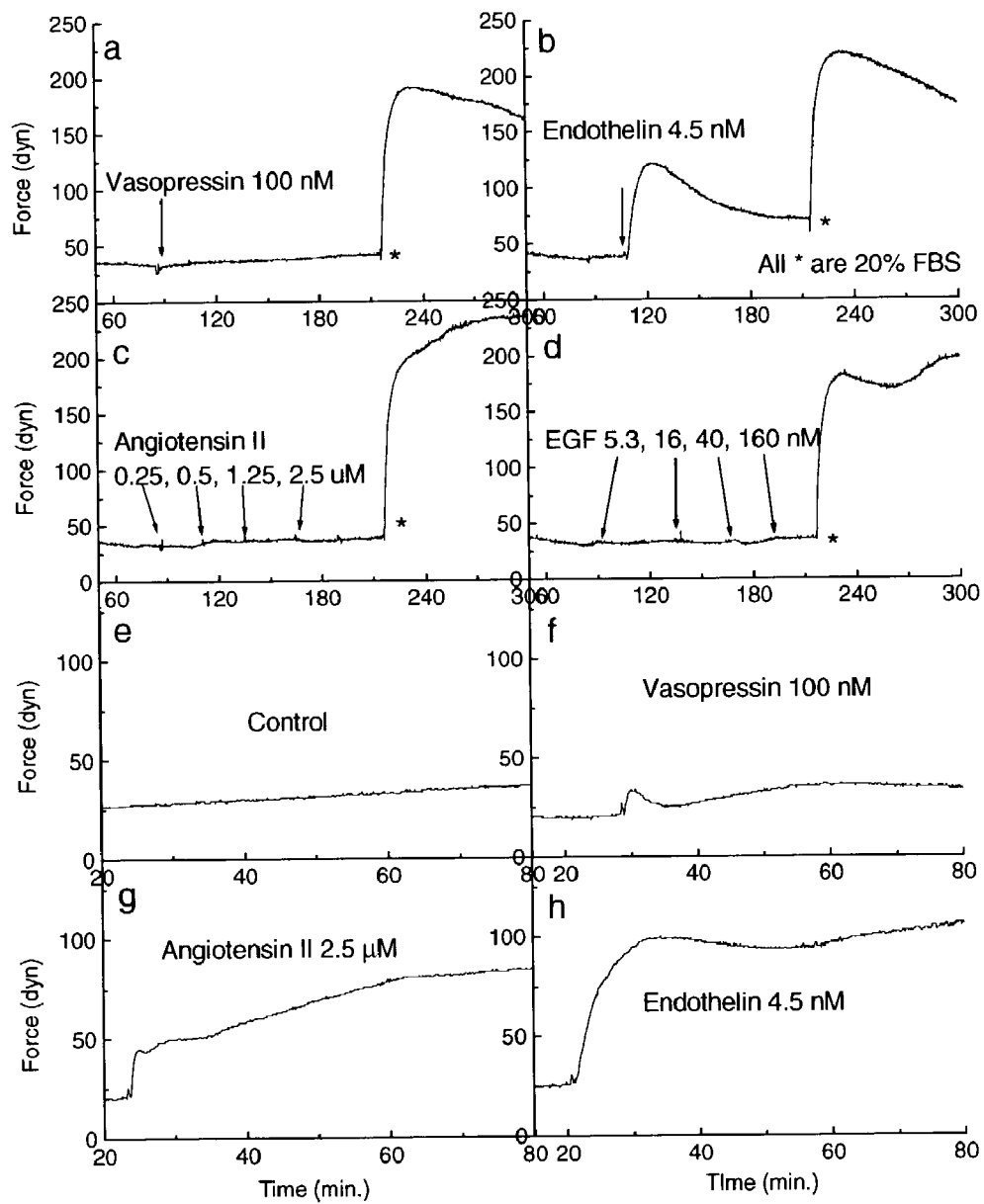

FIG. 16 shows profiles of contractile responses wherein a series of agonists were applied to a tissue model of a ring system made from chicken (panel a-d) and rat (panel e-h) cardiac fibroblasts, respectively.

Figure 17:
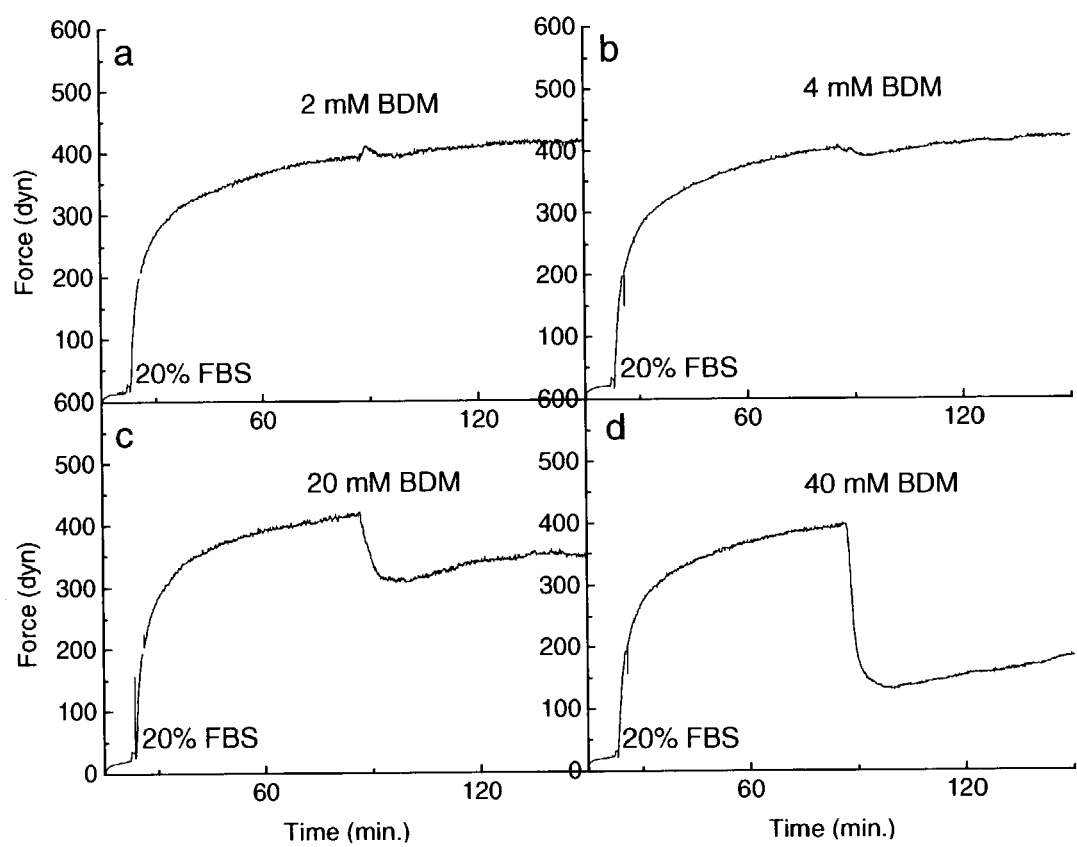

FIG. 17 shows a reduction in contractile force by inhibition of myosin contractility initially stimulated by 20% FBS. FIG. 17 shows the inhibition by different butane dione monoxime ("BDM") concentrations of a contractile response previously stimulated by 20% FBS. Panel a, b, c and d are treated with 2, 4, 20, and 40 μm BDM, respectively.

Figure 18:
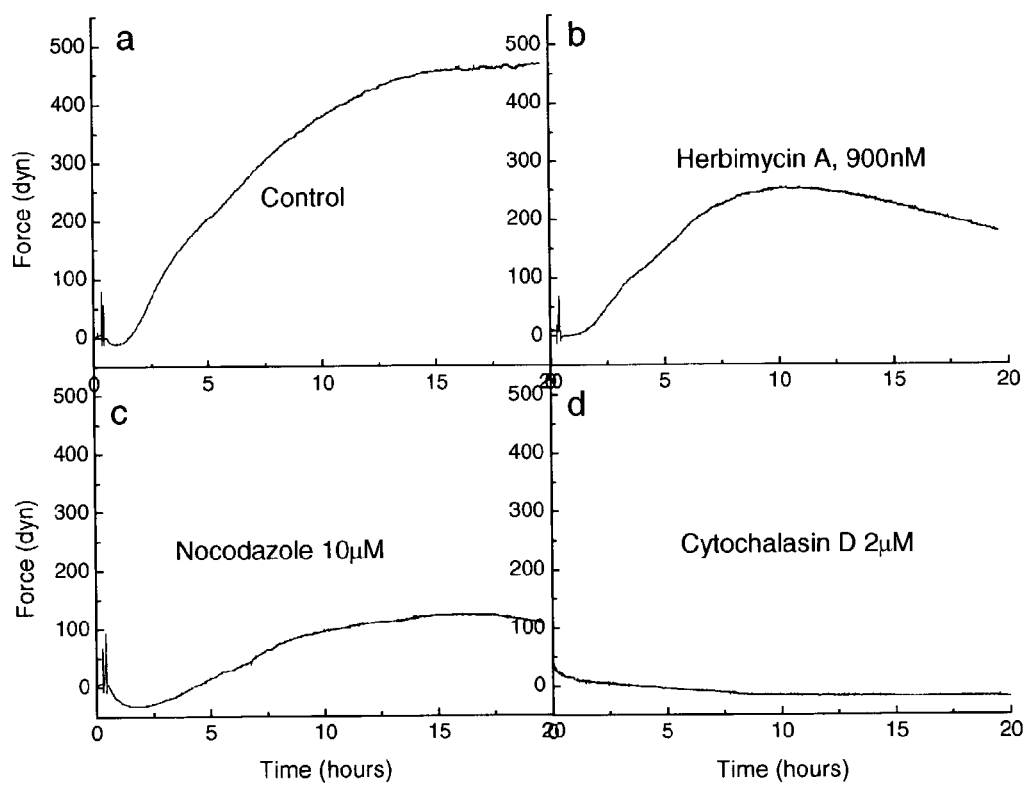

FIG. 18 shows a profile of the increase in contractile force during tissue development in a ring system treated with no chemicals (a), herbimycin A (b), Nacodazole (C), and cytochalasin (D). The ring was mounted on the force measuring system about one hour after gelation of the collagen and prior to significant remodeling and compression of the matrix by the cells.

FIG. 19a shows the dependence of force on strain for a tissue model ring measured after stimulation by FBS (labeled "Total"). The ring was then treated with 2 μM CD and measured to yield the curve labeled "passive". The difference between total and passive is labeled "active." FIG. 19b shows dynamic stiffness derived from the same measurements.

Figure 20:
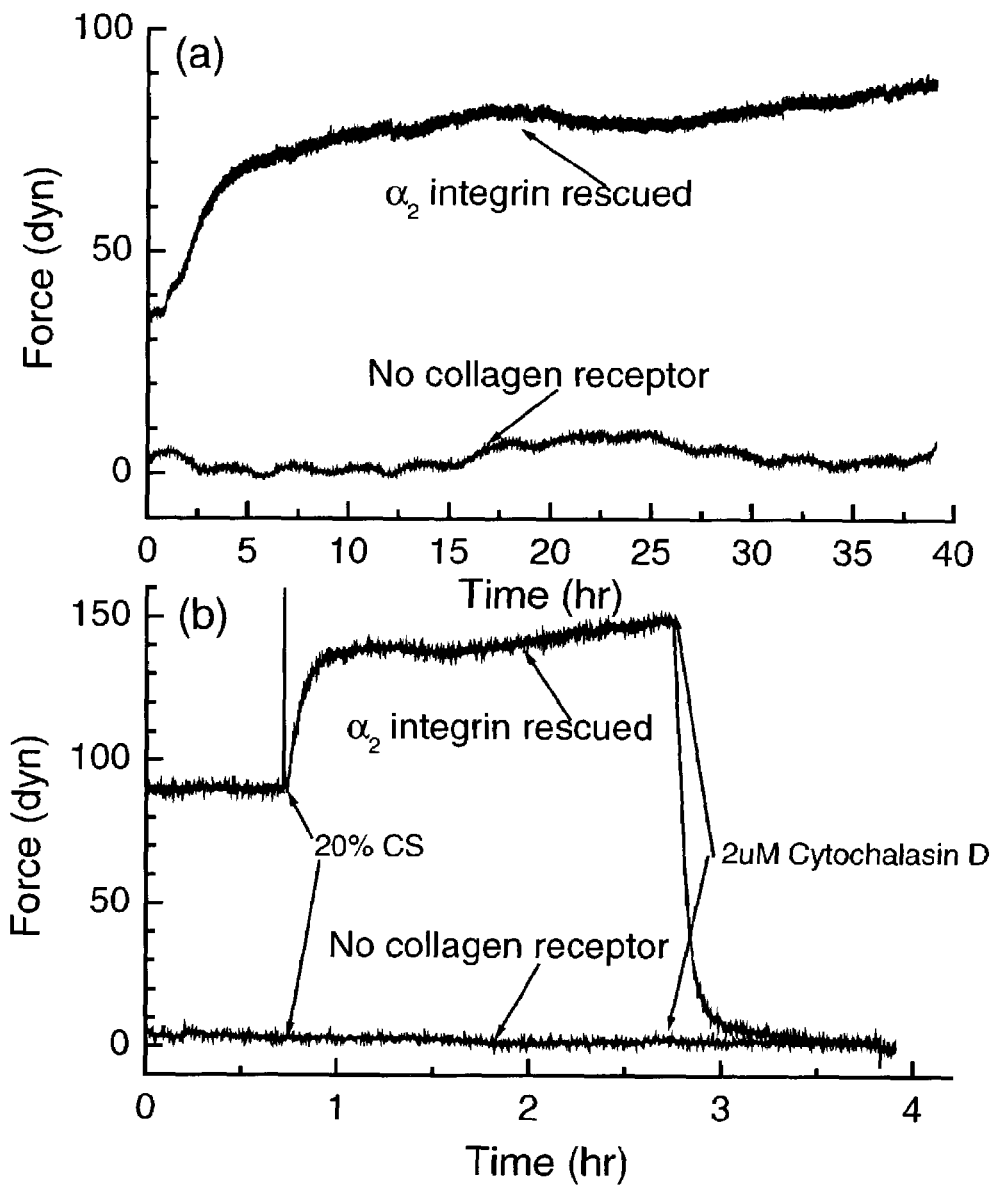

FIG. 20 shows that cells that lack the appropriate collagen-binding integrins can neither develop force during the period of tissue remodeling (FIG. 20a) nor in response to calf serum (FIG. 20b). These defects are corrected by restoring the missing subunit of the collagen binding integrin ($\alpha_2$).

Figure 21:
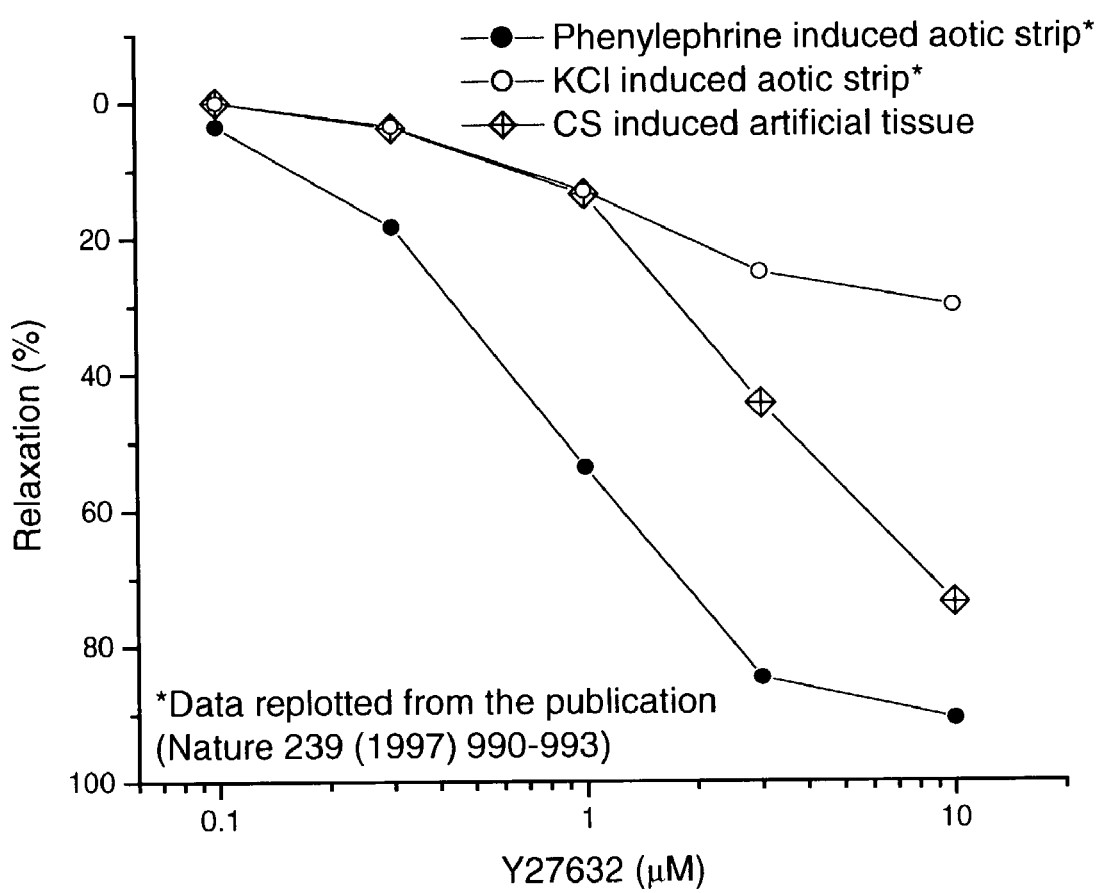

FIG. 21 is a comparison of the change in contractile force after treatment with various concentrations of Y27632, observed using tissue model and artic strips.

Figure 22:
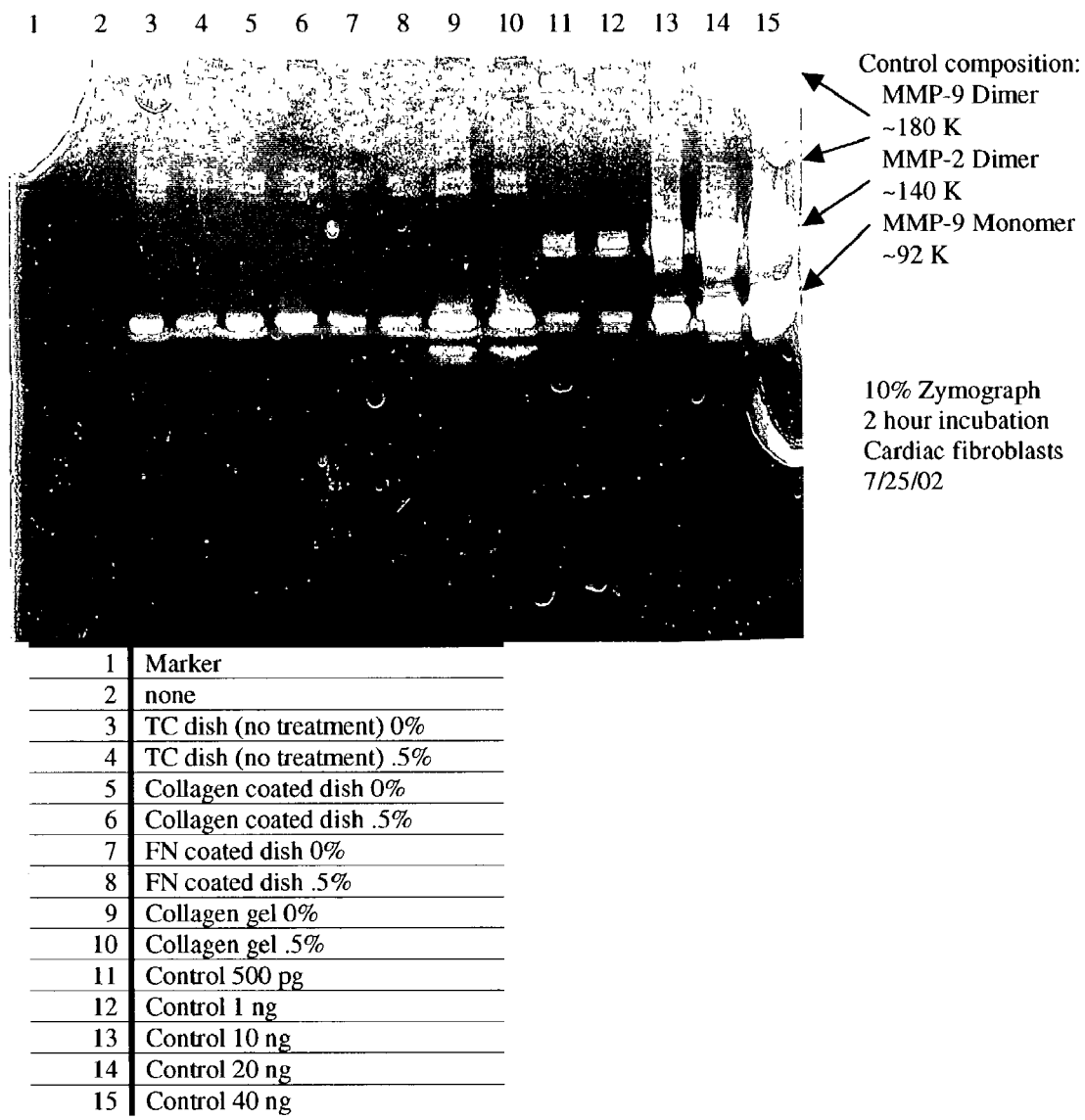

FIG. 22 shows a zymograph of MMPs secreted into the tissue culture medium by cells cultured in various conditions.

Figure 23:
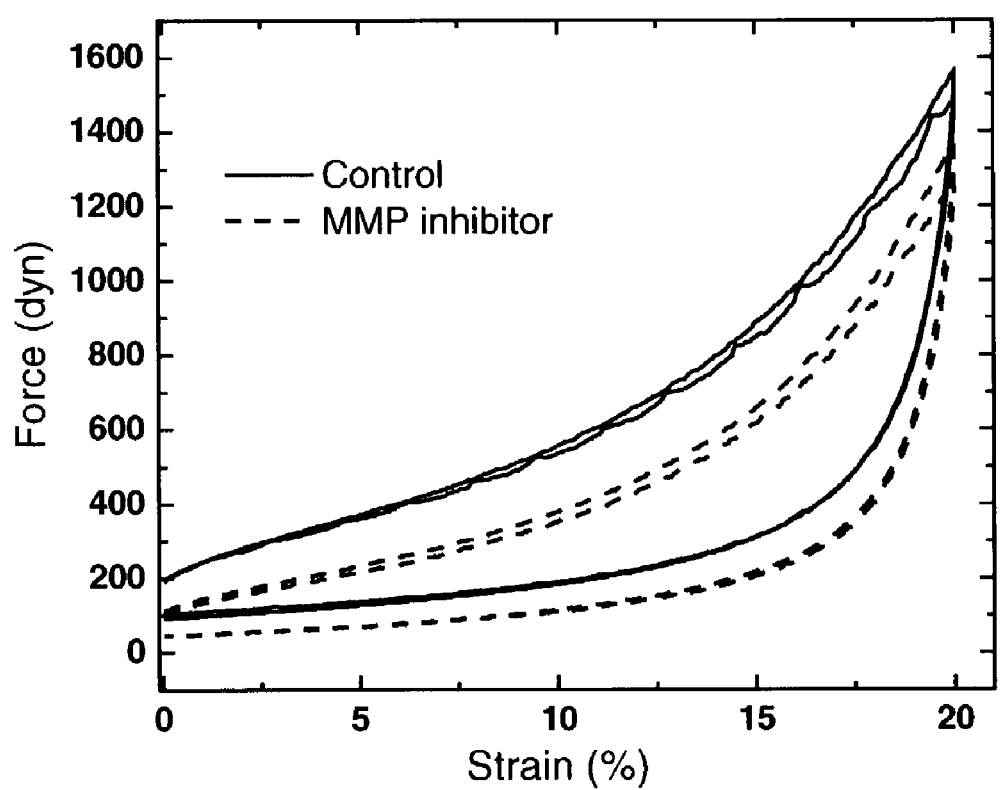

FIG. 23 compares force responses to stretch of tissue models cultured with and without MMP inhibitor GM6001.

Figure 24:
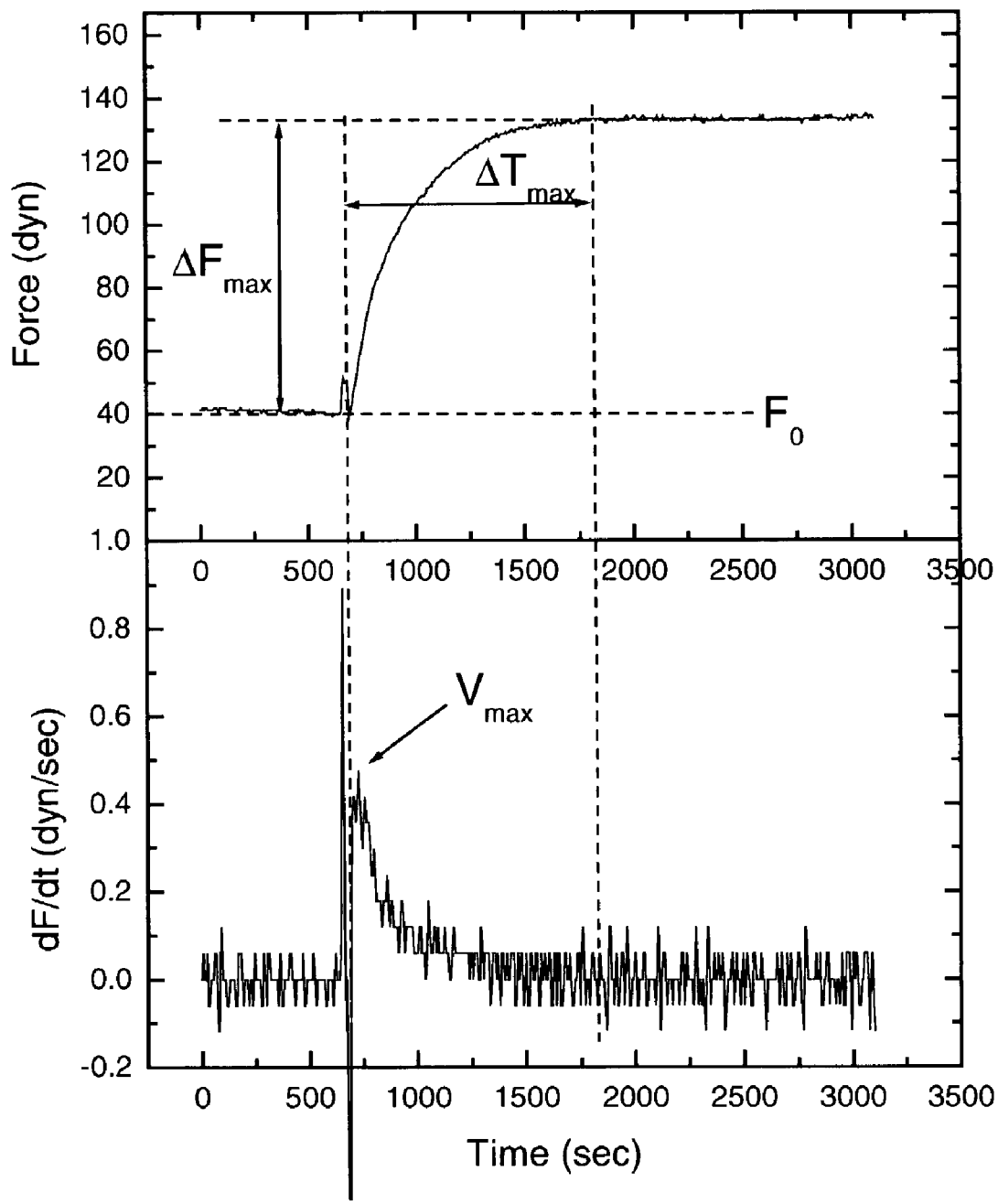

FIG. 24 illustrates the parameters by which the change in force recorded over time in response to various treatments can be represented.

DETAILED DESCRIPTION OF THE INVENTION

There are an estimated 20-30 trillion cells in the human body apportioned among tissues with distinct characteristics and functions. These cells include muscle and non-muscle cells. Muscle cells develop contractile force. Muscle cells respond to nerve signals, which send out messengers such as calcium ion and cyclic AMP that regulate the by generation of contractile force. Non-muscle cells, e.g., fibroblasts and endothelial cells, respond to activators such as a polypeptide growth factor or hormones by generating contractile force.

As used herein the term "treated or contacted with" include exposed to, contacted with and placed in contact with. As used herein, the term "tissue model" includes reconstituted cells and tissues from living cells and extracellular matrix material. As used herein, the term "isometric force" includes the force change without substantial change in the tissue length or tissue physical dimensions. As used herein the term "extracellular matrix (ECM)" includes fibrin, fibronectin, laminin and similar constituents/components and synthetic materials such as polylactic acid and polyglycolic acid.

Tissue models such as the bio-artificial tissue models reconstituted from cells and extracellular matrix (ECM), simulate natural tissues. Such tissue models provide a polydisperse or monodisperse population of living cells in a uniform or substantially uniform collagenous matrix.

Cytoskeletal and matrix proteins control the forces exerted by a tissue model and the stiffness of a tissue model. Cells regulate cystoskeletal structure and remodel ECM to produce mechanical changes during tissue development and wound healing.

Contractile forces result from activation of non-muscle myosin. The increase of contractile force over time after activation can be measured in tissues reconstituted from muscle and non-muscle cells. Such cell responses can lead to reorganization of the cytoskeleton within the cells or of the extracellular matrix (ECM) in which the cells are embedded. The development of contractile forces and the mechanical effects of cytoskeletal and matrix reorganization provide indicators of cellular response to a candidate pharmaceutical(s). Changes of contractile forces and stiffness result from activation or deactivation of cellular myosin, from other cytoskeletal perturbations, or from perturbations of the extracellular matrix within which the cells are embedded.

Use of reconstituted tissue permits assembly of tissue models, which are tested using specifically isolated cell types or in combinations of cell types. Hence, responses of these reconstituted tissues to a candidate pharmaceutical provide mechanical measurements of these cell types without complicating contributions of other cell types normally present in natural tissues. An association is established between a specific cell type and a profile of mechanical measurements of changes of force and stiffness that result when the cells are contacted by an agent.

Contractile force and tissue stiffness change due to contraction and relaxation of the cells within reconstituted tissue upon effective contact with an agent. As used herein the term "agent" includes one or more candidate pharmaceuticals, which may or may not have any pharmaceutical activity or cellular response. Agents also include activators, antagonists and the like. As used herein, the term "effective contact" means placing an effective amount of an activator in contact with the tissue model, for example, as by adding an agent to a tissue model. As used herein the term "pharmaceutical" means having to do with medicine, which affects an animal or a person.

Cells utilized are obtained from a variety of tissue sources so that the tissue models used as tissue systems provide tissue-specific information of responses to candidate pharmaceutical(s).

As used herein, the term "tissue stiffness" is the force required to stretch tissue by a defined amount. In other words, tissue stiffness is the ratio of force applied to the tissue to the extent of stretch of the tissue. The force required to stretch an elastic object increases as the extent of stretching of the object (the "strain") increases. Biological tissues, however, are viscoelastic. That is, viscous forces that depend on the rate of stretching also contribute to resistance to stretch. Measurements of the contribution of viscous forces may be determined from the dependence of the stiffness on the rate of stretching. For linearly elastic materials the force increases linearly with strain, i.e. stiffness is constant, independent of strain. Biological tissues and reconstituted tissue models are mechanically nonlinear and tissue stiffness increases with strain. Over a range of forces the stiffness varies linearly with the force either generated within the tissue or externally applied to it. This linear variation indicates that the force is an exponential function of strain.

One method of measuring tissue stiffness includes subjecting the tissue in a tissue model system to a relatively large steady stretch and observing the change in force as the strain increases. Such measurements of tissue stiffness enable measurements and determinations of parameters including hysteresis (area), phase lag and dynamic stiffness.

Once a preset strain is achieved during the measurement of tissue stiffness, the extent of stretching (strain) can then be reduced at the same rate in a return to the tissue's initial strain and stiffness values. A plot of force as a function of strain as strain decreases (unloading curve) is always at lower force levels than during the increase of strain (loading curve). The area enclosed by the aforementioned two curves is a hysteresis area, which is an indicator of tissue viscosity. The hysteresis area measures a loss of energy in the tissue during the respective loading-unloading cycle.

Another method of measuring tissue stiffness uses oscillatory stretch, i.e., periodic increases and decreases of strain at a defined frequency (e.g. sinusoidal) selected by an experimenter. The force increases and decreases correspondingly at the same frequency, but possibly with a shift in phase, i.e. a phase lag. The phase shift or phase lag is another indicator of the viscosity of the tissue models. The type of tissue stiffness measured by oscillatory stretch is "dynamic stiffness". Dynamic stiffness depends on the magnitude of the stretch (because tissue models are nonlinear) and on the frequency of oscillation because the tissues are effectively viscous.

In illustrative embodiments of this invention mechanical measurements are carried out on reconstituted tissue models. The invention provides a method of quantitatively characterizing mechanical properties of connective tissue models, such as fibroblast-populated matrices (FPM's), via uniaxial stretch measurements in response to contact with one or more activators.

The connective tissue models, which are composites of selected living cells and ECM (i.e. a bio-artificial system), usually Type I collagen, respond by stiffening due to contact with activators which activate contractile forces. In one embodiment illustrative of a tissue model system of this invention, the tissue is assembled in the form of a ring that is mounted on a system in which the tissue spans an isometric force transducer and a computer-controlled stepping motor for measurements of contractile force and strain.

In another embodiment of this invention, especially suitable for high throughput screening, tissue stiffening is measured by an indentation method using a multi-well plate system. In the indentation method, contractile force is measured (as peak force) along with tissue stiffness, which is registered as a resistance to indentation of the tissue model by a probe contacting the tissue model. The probe is attached to a force transducer. Many tissue composites can be rapidly tested (high throughput) for their mechanical responses to reagents in this embodiment. The system is suitably adapted in size and design to use small amounts of tissue model and reagents.

Candidate pharmaceuticals that inhibit a contractile response can be screened for their ability to prevent a stiffening response evoked by a well characterized activating agent. Moreover, candidate pharmaceuticals that cause cells to remodel the collagen, thereby stiffening or softening the collagen, can be tested using the inventive methods disclosed herein.

This invention provides a system and method for characterizing and profiling the mechanical response(s) of reconstituted tissue models in contact with one or more agents. The invention allows rapid and quantitative screening of many potential activators or inhibitors of cell contraction, cytoskeletal change, cell-matrix interactions, and matrix remodeling. The methods herein provide a quantitative readout of changes in tissue stiffness, which can be calibrated to supply corresponding quantitative data on the extent of activation or inhibition of myosinmodulation of cytoskeleton components or of interaction of cell-matrix and properties of the matrix itself.

The systems and methods described and claimed herein are not limited to the specific embodiments described herein. In addition, components of each system and each method can be practiced independently and separately from other components and methods described herein. Each component and method can be used in combination with other components and other methods.

Collagens useful include collagen Classes 1-4 which include all Types I-XIII and combinations thereof Agents useful as activators include Fetal Bovine Serum (FBS), lysophosphatidic Acid (LPA); thrombin, growth factors including epidermal growth factor (EGF), platelet derived growth factor (PDGF), angotensin-II, endothelin-1 and vasopressin and combinations thereof.

Inhibitors include those inhibitors which act on cell surface receptors including a receptor antagonist for angiotensin IIreceptor and also inhibitors that act within the cell. Inhibitors useful herein include those which inhibit the process of signal transduction pathways including genistein, herbimycin and agents which act on the cytoskeleton. These include cytochalasin D, latrunclin B, paclitoxol, nocodazole, calyculin A and butane-dione-monoxime (BDM) and combinations thereof.

The amount of agent(s) provided to the reconstituted cell is an effective amount which is generally from an amount in nanomolar quantity to an amount of about 100 millimolar. An effective amount is that amount which is sufficient to elicit a response from or by a tissue model.

There are several mechanical parameters which may be determined using embodiments of this invention.

| Ring type system: | |
|---|---|
| Baseline force | Force measured at 0 strain (no stretch). |
| Dynamic stiffness | Amplitude of force response to the sinusoidal stretch divided by amplitude of applied oscillatory strain. The measurements are taken at various strain levels. Dynamic stiffness can also be obtained during a ramp stretch. |
| Phase angle | Phase angle indicates time dependent viscosity of a sample. It is obtained by the angle of phase delayed between force response and sinusoidal driving function. The measurements are normally taken at 0 strain but can be measured at various strains as long as the mean force level reaches a steady state for a short period of time. |
| *Storage modulus, G' | In-phase component stress (force divided by cross sectional area of sample) in response to a sinusoidal stretch divided by the strain. |
| *Loss modulus, G" | Out-of-phase component stress in response to a sinusoidal stretch divided by the strain. |
| Peak force | Peak force in response to a ramp stretch. |
| Hysteresis curve area | Hysteresis curve is a plot of force response to a ramp stretch plotted against strain. Force response during the sample elongation is always higher than that during the sample shortening. The area enclosed by the two lines is related to the viscosity of the sample. |
| Tissue Indentation procedure: | |
| Peak force | Peak force in response to tissue indentation. |
| Hysteresis curve, area | Hysteresis curve is a plot of force response to a tissue indentation. Force response during the indentation (loading) is always higher than that during the retraction (unloading). The area enclosed by the two curves is related to the viscosity of the sample. |

*G' and G" can be calculated from dynamic stiffness and phase angle by knowing the cross sectional area of samples. G' and G" are parameters indicating the mechanical properties of samples independent of their sizes and shapes.

More details are set forth below regarding FIGS. 1-15. Although specific exemplary embodiments of methods and systems for using tissue models are described herein, the methods and systems are not limited to such specific exemplary embodiments.

Figure 1:
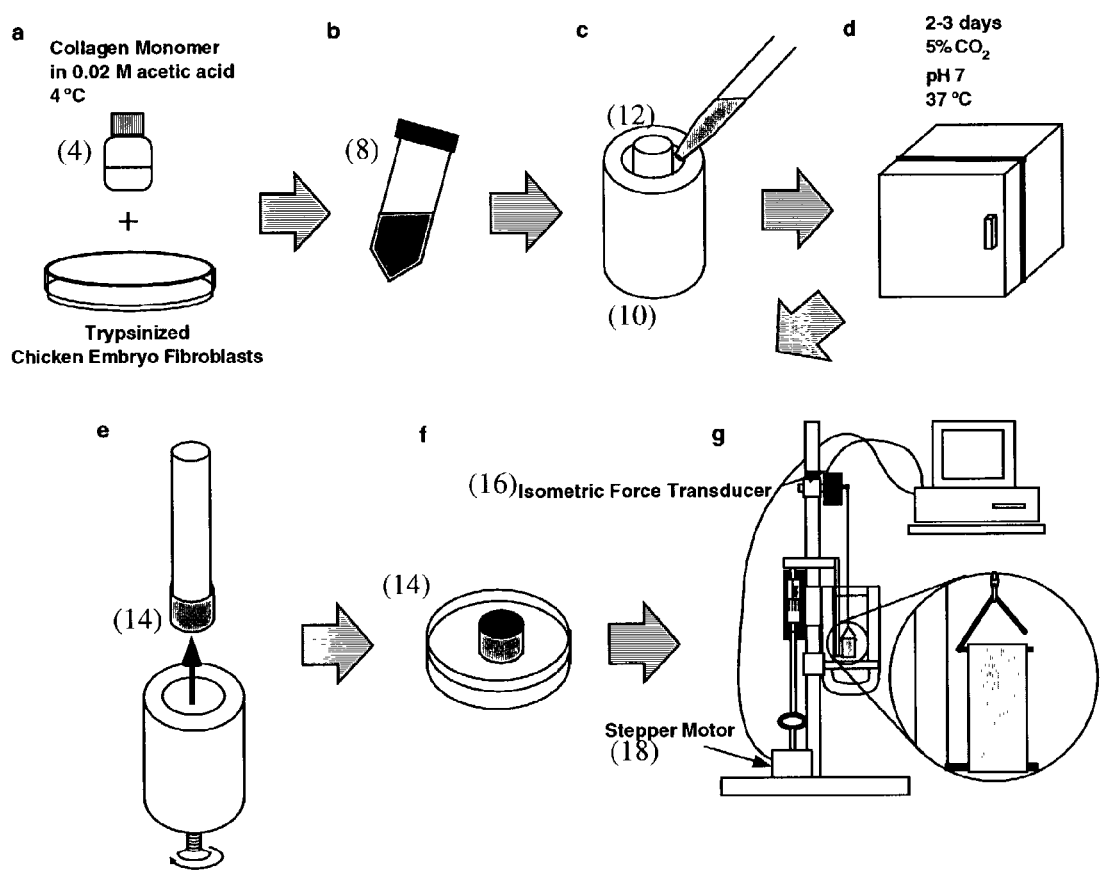
FIG. 1 is a schematic of an illustrative method for preparing and measuring fibroblast populated matrices (FPMs) (including live tissue models).

More in particular, FIG. 1 is an illustrative schematic of a ring method for preparing and measuring FPM's (illustratively shaped as a ring). In an embodiment, CEF's (2) and monomeric collagen (4) are mixed in DMEM (6) at pH 7 to form a suspension (8). This suspension (8) is poured into casting wells (10) having a mandrel (12) and polymerized at 37° C. The casting wells (10) are incubated for a day or more during which time the cells compress and remodel the polymerized collagen matrix. After incubation the mandrel (12) is removed from the casting well (10) and the FPM-ring (14) is removed gently from the mandrel (12). The FPM-ring (14) is connected to the force measuring apparatus (an isometric force transducer) (16) and a stepper motor (18) that controls and sets the tissue strain.

Figure 2:
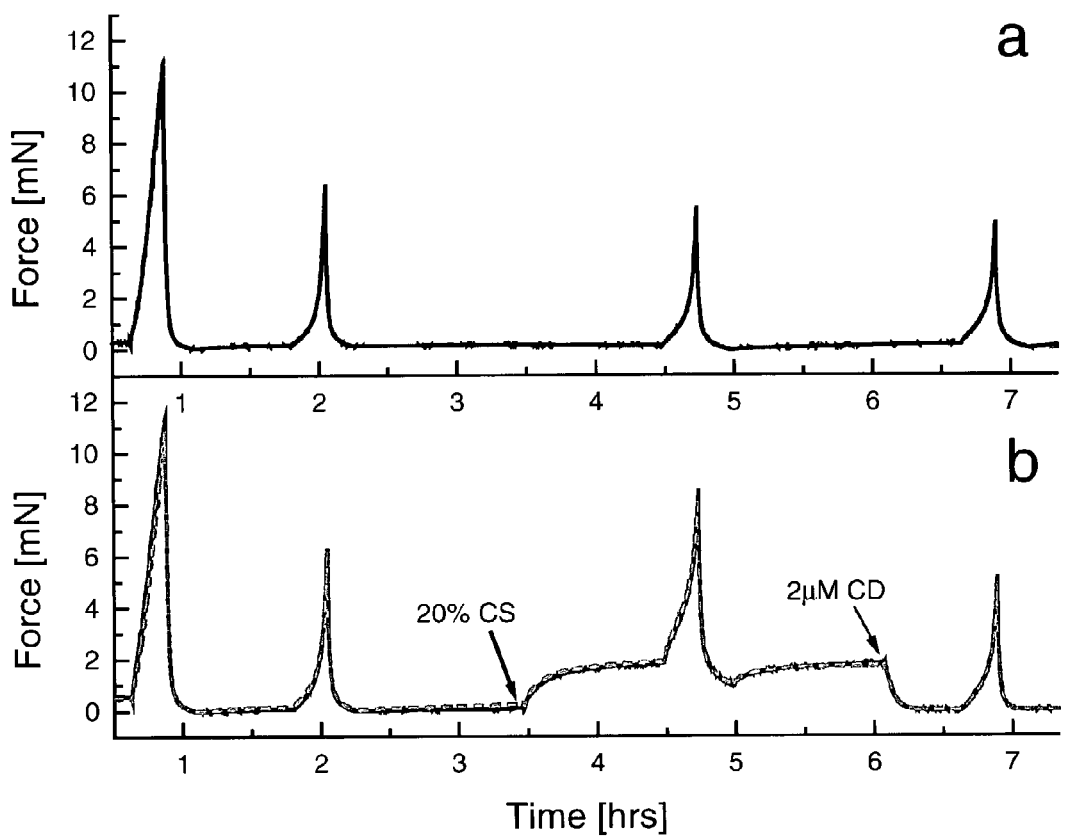
FIG. 2 illustrates a force response to stretch from a tissue model and illustrates a profile obtained from a sequence of four stretch cycles applied to one FPM plotted over time. Profile a of FIG. 2 illustrates a substantially larger peak force for a first stretch than for subsequent cycles. Profile b of FIG. 2 illustrates the excellent reproducibility of the measurements by showing force responses of measurements carried out on two FPM's.

FIG. 2 depicts how measured a force respondsive to stretch of a FPM. Typical force responses from a sequence of four stretch cycles applied to one FPM were traced in time. The first stretch cycle (as shown in panel a) produces a substantially larger peak force than subsequent cycles. A much smaller (~6%) reduction in peak force is seen in each of the subsequent cycles (panel a). Panel b of FIG. 2 illustrates the reproducibility of the measurement by showing stretch sequences form two FPM's. (solid . . . ) (solid line and gray broken line). The effects of treatment by both 20% calf serum (increase in contractility) and 2 uM Cytochalasin D (abolition of active contractility of the tissue) are almost identical. The cycle time was set to 30 minutes instead of the previously used 60 minutes cycle time for this test to accommodate additional test manipulations. (The force-strain and stiffness-strain curves from the 30 and the 60 minute cycle times, however, are almost identical.)

Figure 3:
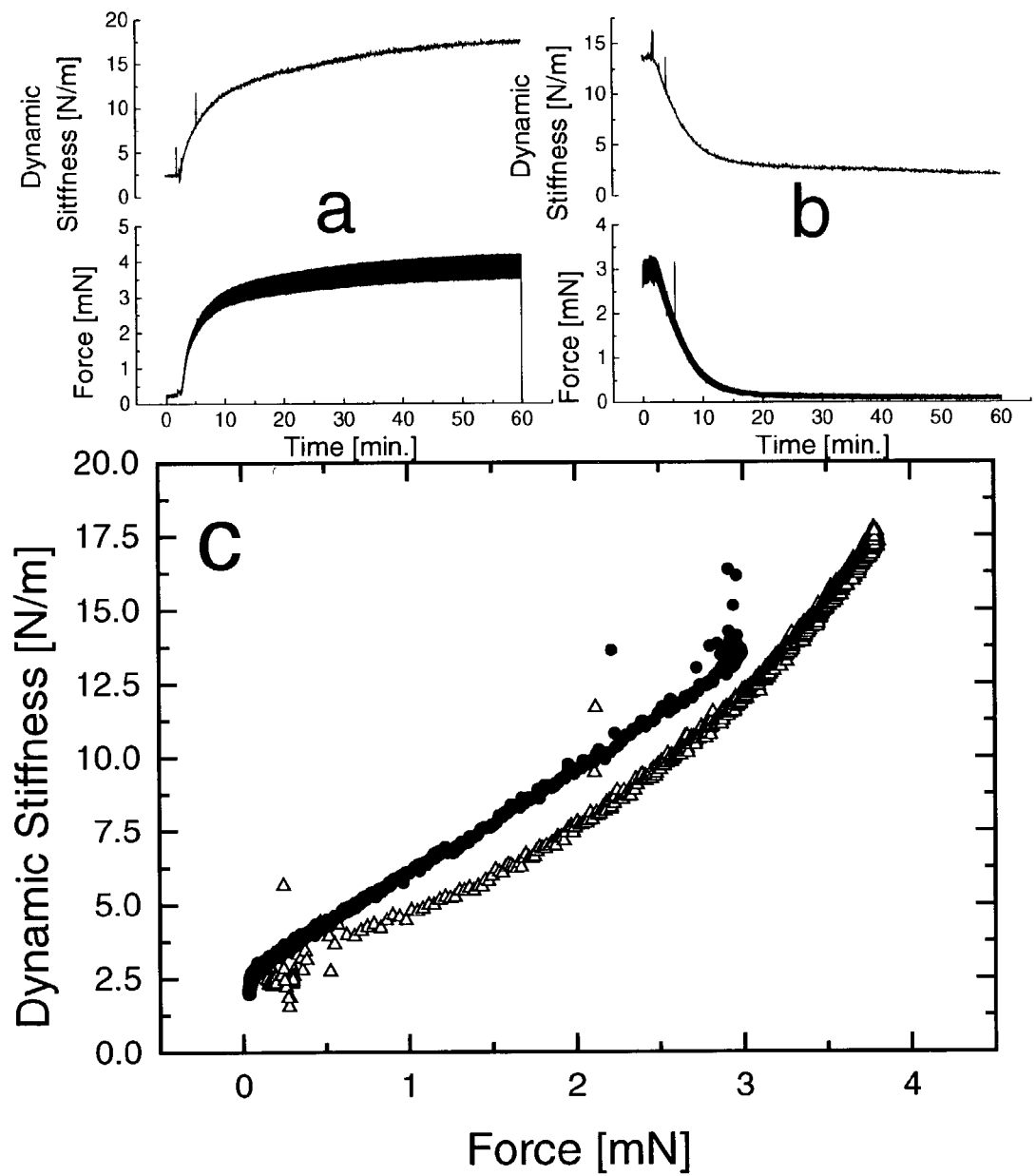
FIG. 3 is a graph, which displays tissue stiffness as a function of cell generated force.

FIG. 3 shows data of measured stiffness as compared to cell-generated force. In this test, the tissue model was stretched sinusoidally by 0.3% at 1 Herz. The stiffness was measured as the peak-to-peak change in the force (approximated by the breadth of the trace at this time scale). Each stiffness point represents the average stiffness for 5 seconds.

FIG. 3, graph (A) shows that stiffness changes with a magnitude and time course similar to force during FBS (5%) stimulation. FIG. 3, graph (B) shows actin filament disruption by Cytochalasin D (2 μM). As in FIG. 3 (A) stiffness changes correspond to force changes.

FIG. 3, graph (C) shows stiffness plotted against force for measurement data shown in FIG. 3 parts (A) and (B). The force-stiffness relation for the rise in force after FBS (closed circles) is very similar to the force-stiffness relationship for the decline in force after addition of Cytochalasin D (open triangles). Each circle point and triangle point of this Figure represents both force and stiffness. Stiffness increases approximately linearly with force.

Figure 4:
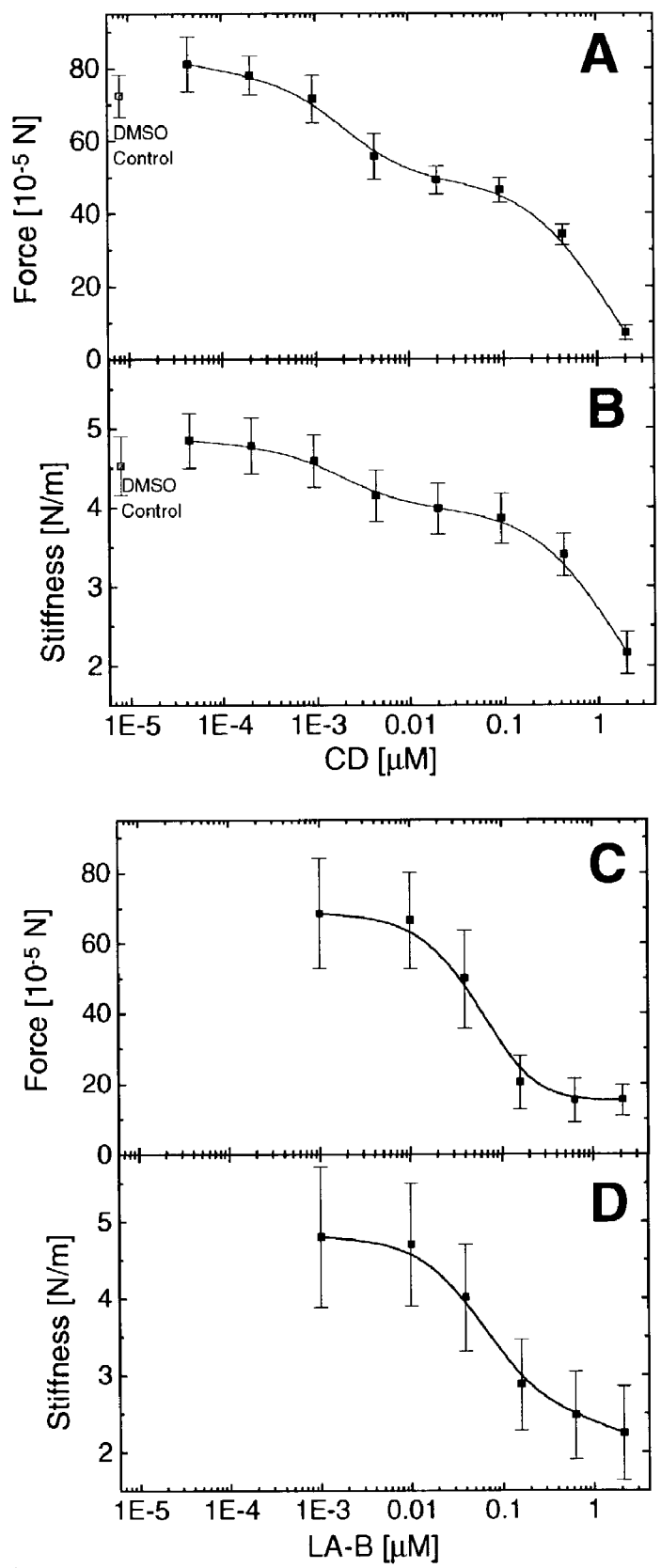
FIG. 4 displays a dependence of contractile force and dynamic stiffness on CD and Latrunculin B (LA-B, Calbiochem-Novabiochem Corporation, San Diego, Calif.) concentrations.

FIG. 4 illustrates the dependence of force and dynamic stiffness on CD and LA-B concentrations. The force and dynamic stiffness were significantly diminished at a CD concentration of 2 nM and continued to fall as the CD concentration was increased (A, B). In contrast, for LA-B the force and dynamic stiffness began to diminish only when the concentration reached 40 nM, and reached their minimum values at a concentration of 600 nM (C, D). This Figure illustrates the sensitivity of the measurement method, which can detect force and stiffness changes at low concentrations of CD that cause no changes in the actin cytoskeleton which can be detected by light microscopy.

FIG. 5 illustrates a comparison of data variance in tissue model stiffness measured using reconstituted tissues with a ring method (left bar graph) and in cell stiffness measured by indentation of individual cells (right bar graph). Reconstituted tissue can provide statistically significant data with less data points as compared to single cell measurements. Fewer measurements are required to obtain statistically significant data using tissue models than using single cells. This is because, even in a cultured population of cells of a single type, there is substantial cell-to-cell variation for many experimental parameters. Hence, measurements on many individual cells must be averaged to characterize the population. Therefore high throughput screening devices that measure the biological activity of chemical compounds on single cells require many measurements to obtain statistically significant data. Since the tissue models tested contained at least 10,000 cells, each measurement represents an average of many cells in the tissue. Therefore, the efficiency of high throughput screening on tissue models is improved over that on single cells.

Figure 11:
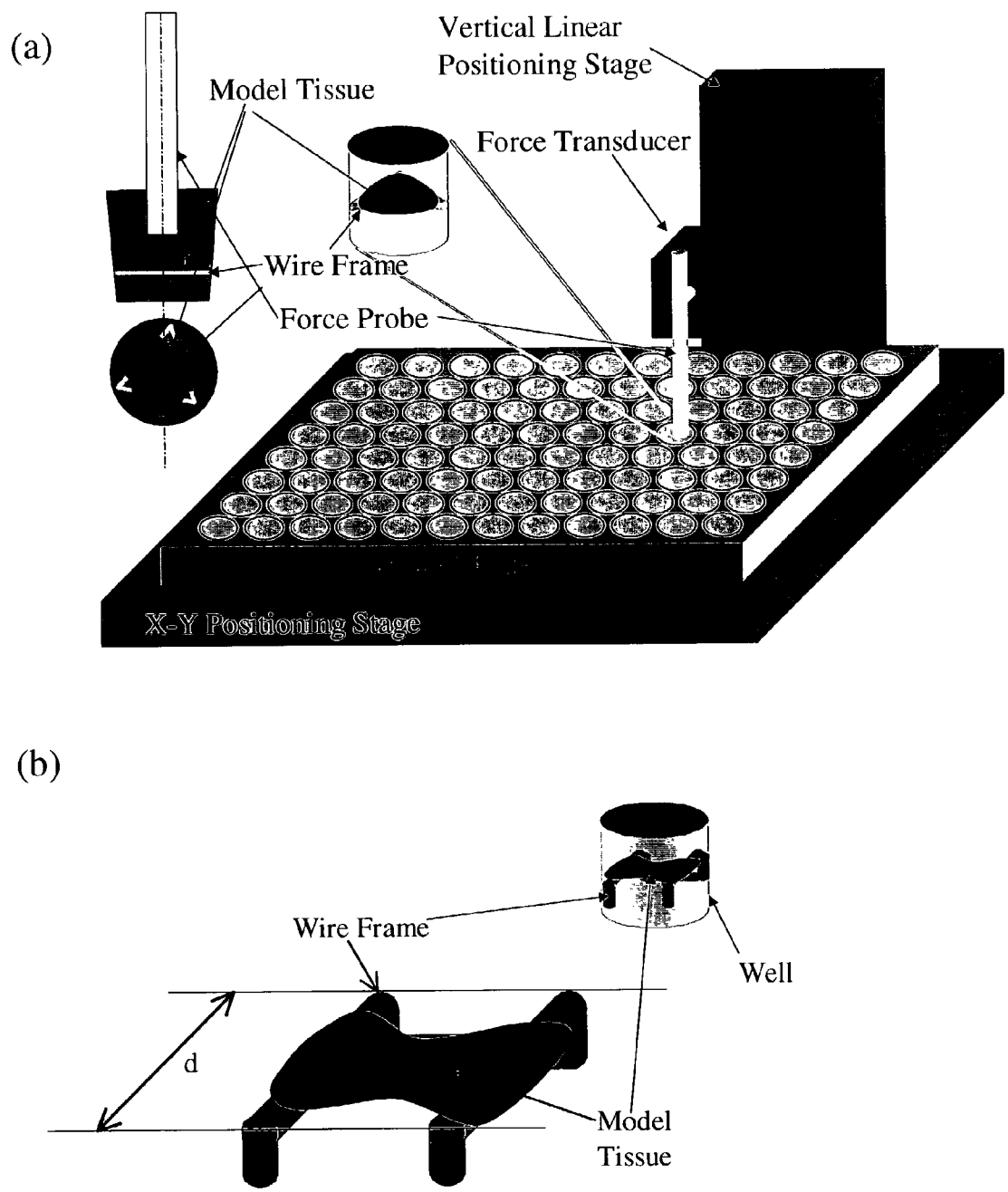
FIG. 11a shows a high throughput system illustrating use of triangular and rectangular (alternative shape) frames shown in FIG. 11b, made of stainless steel wire about one millimeter in diameter, which provide scaffold supports on which reconstituted tissues form to provide samples from an indentation method of measuring tissue contractile force and stiffness.

FIG. 11 illustrates an exemplary high throughput screening system utilizing an indentation method for measuring the mechanical response of this tissue system.

A triangular frame made of stainless steel wire one millimeter in diameter provides a scaffold on which reconstituted tissue forms. In this illustration, the wells are slightly tapered toward the bottom and the frame is securely positioned 1 mm above the bottom of the well (The non-polymerized solution of collagen containing cells and appropriate cell culture media as described above was poured into the wells filling them to a level 3 mm above the bottom (FIG. 11a). The 96-well plate was incubated at 37° C. with 5% $CO_2$. During incubation, the cells compress the collagen matrix by squeezing out liquid thereby reducing the total volume by about ten fold.

Without the wire frame, the reconstituted tissue contracted into a small sphere floating in the tissue culture medium. The collagen matrix can be compressed into different shapes using different frame shapes such as a circle or rectangle shapes of a support such as a wire frame. The support can be one of metal, nonmetal, and plastic. In an embodiment, system is a self assembly cell system in which cells form a tissue model conforming to the shape of a frame or support.

On a triangular wire frame the cells form a membrane spanning among the three edges, which is illustrated in FIG. 11a. Other wire frame shapes, such as one shown in FIG. 11b, produced tissue strips with different widths and shapes. A porous support material such as a Velcro fastener was not utilized to facilitate tissue adhesion even to the non-porous stainless steel surfaces of the wire. The collagen was compressed to a greater extent at the outer portion of the membrane or strip. Therefore, this outer portion of the membrane can withstand the stress produced by the cells and prevent the stress ripping the membrane off from the wire frame.

Figure 12:
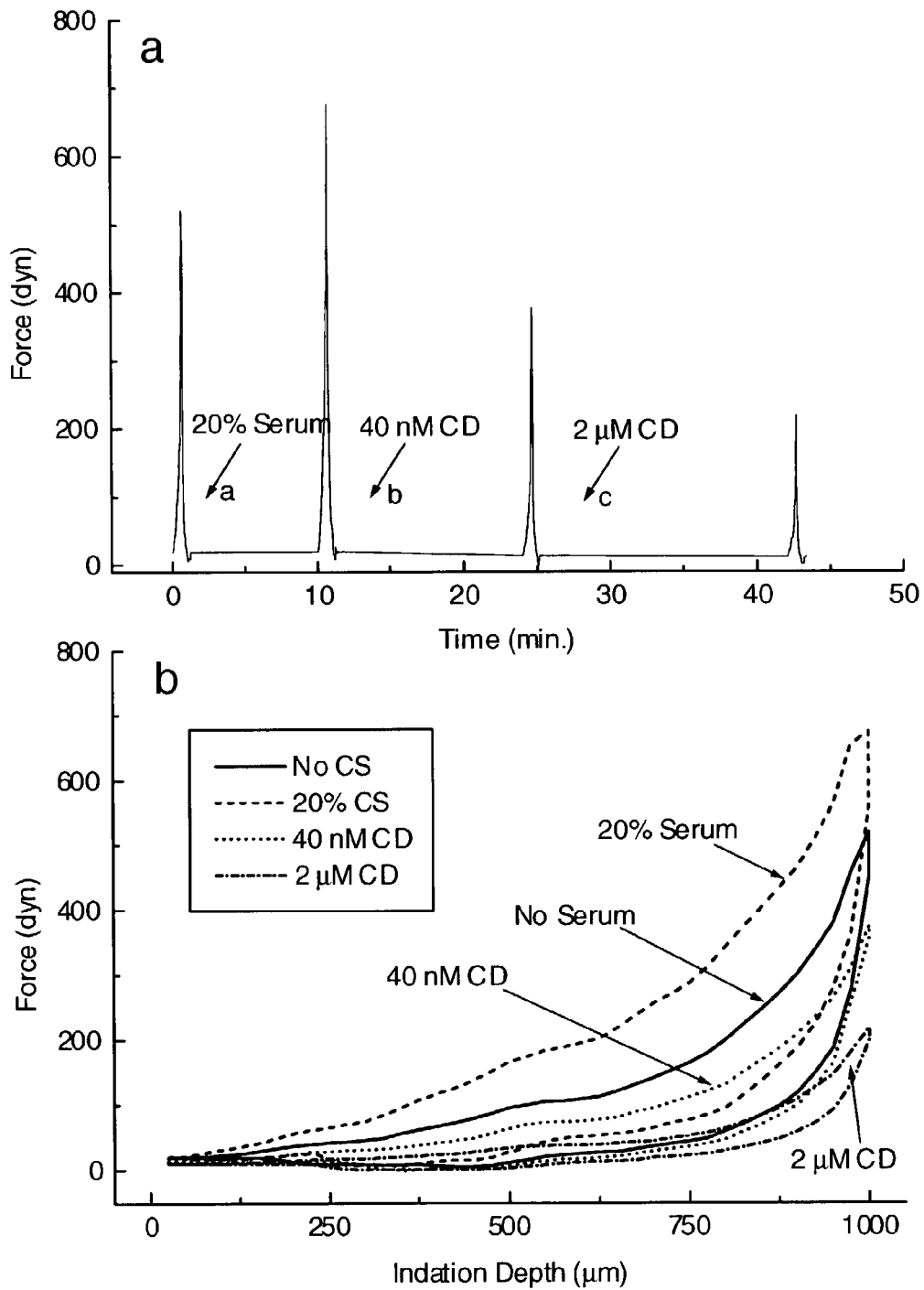
FIG. 12 shows that after the peak contractile force reaches its steady level the tissue model is activated with 20% Fetal Bovine Serum (FBS) (arrow a in FIG. 12(a) to cause an increase in force. This amount of FBS activates fibroblast non-muscle myosin.

FIG. 12 shows data taken using the system exemplified in FIG. 11 above. The data shows that after the peak force reaches its steady level the sample is stimulated with 20% Fetal Bovine Serum (FBS) (see arrow a in FIG. 12a). This amount of FBS activates fibroblast non-muscle myosin producing a contractile force that stiffens the reconstituted tissues. At about 10 minutes after the FBS addition, there is about a 25% increase in the peak force of subsequent indentations (FIG. 12a). Nearly 15 minutes after the addition to the medium of 40 nM CD (see arrow b of this figure), the peak force from subsequent indentations has decreased about 40% from its initial level (FIG. 12). A further reduction of peak force was recorded 20 minutes after addition of 2 μM CD. FIG. 12(b) is a plot of the same data as the data plot shown in FIG. 12(a), but FIG. 12(b) shows force versus indentation depth for the same conditions as for FIG. 12(a).

Figure 13:
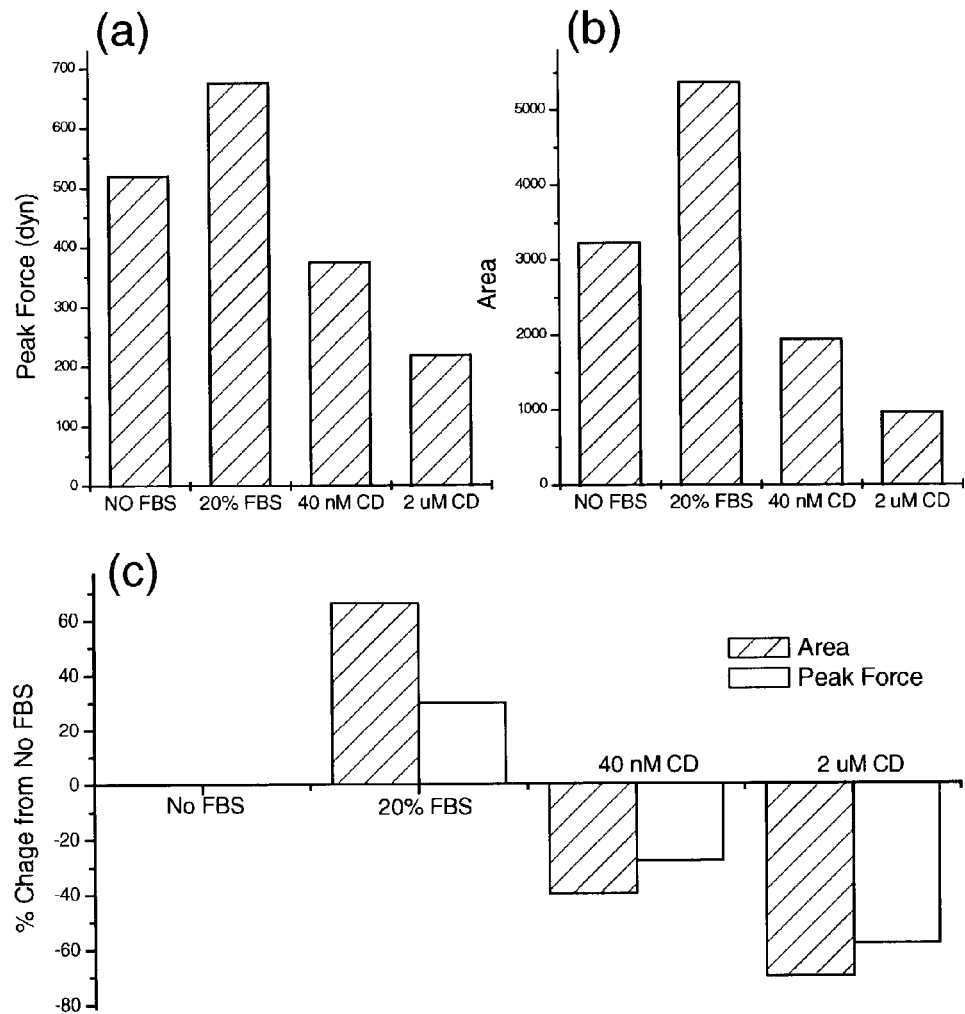
FIGS. 13(a), 13(b) and 13(c) show changes in the peak tissue contractile force and area (arbitrary unit) of hysteresis as relates to FIG. 12.

FIG. 13 is a comparison of percent changes in the peak force and area of hysteresis during the test which generated the data of FIG. 12 shown above. FIG. 13(a) shows the peak force (dynes) measured prior to FBS treatment (no FBS) after 20% FBS, after 40 nMCD and after 2 μMCD. FIG. 13(c) shows the corresponding changes in peak force and hysteresis relative to the values obtained prior to FBS treatment.

The area of hysteresis changes to a greater extent upon stimulation and CD addition. Therefore, the area of hysteresis is a more sensitive parameter than the peak force for monitoring the changes in mechanical properties of the tissue model.

Figure 14:
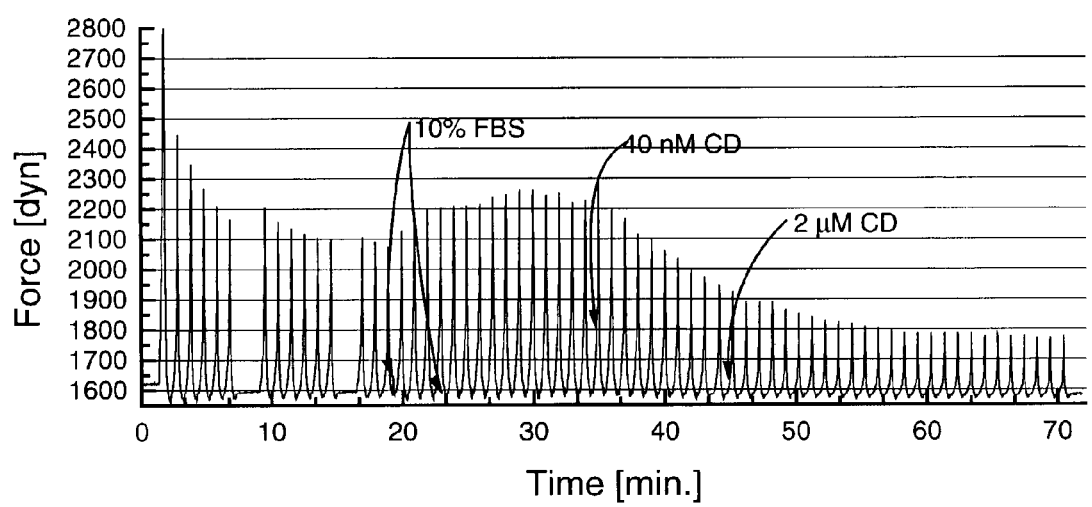
FIG. 14 illustrates a series of force responses to indentations on reconstituted tissue membranes. A small membrane in a well of a 96-well plate was repeatedly indented (each peak represents one indentation.) Force responses to the indentations were recorded over 70 minutes. Peaks of indentation increased due to activation of myosin by addition of 10% FBS, whereas cytochalasin D (CD) reduced peaks in a dose dependent manner by disrupting the actin cytoskeleton. (Force scale was not offset to zero.)

FIG. 14 shows measurements of the mechanical properties of a miniaturized reconstituted tissue using a 96-well plate. The system can be used for high throughput screening since it allows rapid and parallel measurements using the multi-well plate.

FIG. 14 shows the force trace of mechanical measurements conducted using 96-well plates. A small membrane of reconstituted tissue is supported by a stainless steel wire frame. A vertical bar attached to an isometric force transducer indents the membrane and measures the force resisting the indentation. The addition of 10% FBS increases the force peak's height by 30%. The addition of CD reduced the height of the peaks by 60%.

By automating the procedures using the 96-well plate system or going to an even higher degree of parallelism, the basic concept can be expanded to high throughput applications using the invention. Libraries of compounds can be screened and managed based on their biological activities using tissue models.

Typically, contractile force increases rapidly over a period of a few minutes following contact of an agent with a tissue model system. The contractile force reaches a maximum value and after reaching that maximum value the contractile force may be sustained over a period of an hour or more or the contractile force may decline at a rate that is specific to the activator and a cell type. The reason for the relaxation of the force is not critical but this produces further information and data for characterization of force and stiffness response.

During activation, different pathways, involving specific sets of enzymes and co-activators, which can vary among different activating agents, carry the signal received at a cell surface receptor into the cell to activate contractile force. Hence, the development and maintenance of contractile force provides an indicator (or profile) of specific cellular responses to contact with exogenous activators and to the operation of transduction pathways from cell surface receptors to the activation of myosin. The profile for non-muscle cells includes the maximum contractile force value and the maintenance of the contractile force over time.

The invention is further described in the following examples which is not intended to limit or restrict the invention in any way.

EXAMPLES

Preparation of Tissue Models

Bio-artificial living tissue models were prepared which were reconstituted from cells and extracellular matrix (ECM). These models simulate natural tissues.

Chicken embryo fibroblasts (CEF's) isolated from 11-day chicken embryos (Spafas Inc., Preston, Conn.) were maintained in Dulbecco's modified Eagle's medium (DMEM) supplemented with 10% fetal calf serum (FCS), penicillin at 50 units/ml, and streptomycin at 50 microgram/milliliter. The CEF's used to make tissue models were passaged once or twice from primary cultures. Monomeric collagen solubilized in 0.02 M acetic acid (Upstate Biotechnology Inc., Lake Placid, N.Y.) was neutralized at 4° C. with 0.1 N NaOH and mixed with concentrated DMEM stock to yield a final normal DMEM concentration. The fibroblasts suspended by trypsin (FIG. 1a) were mixed with the collagen solution (FIG. 1b), the cell suspension was poured into Teflon casting wells (FIG. 1c), and the wells were incubated at 37° C. with 5% $CO_2$ (FIG. 1d). The collagen polymerized within 15-30 min and fibroblasts were captured within the hydrated collagen gel. The collagen gel formed a ring (3 mm thick, 3 cm diameter) between the inner wall of the cylindrical well and the central mandrel. While in culture the cells compressed this ring, reducing its volume about 10-fold (thickness 200-300 µm). The ring could then be removed from the mandrel (FIG. 1e and FIG. 1f) and mounted on the measuring instrument (FIG. 1g) as described below.

The types of cells that can be used to form reconstituted tissues are not limited to CEF. Cell types that have been used to form suitable tissues for mechanical measurements include chicken embryo fibroblasts, chicken embryo cardiac fibroblasts, chicken embryo cardiac myocytes, rat cardiac fibroblasts, mouse myotubes, mouse skeletal muscle $C_2/C_{12}$ cell line, normal mouse mammary gland (NMuMG) cell line and its mutant lines lacking $\alpha_1$ and $\alpha_2$ integrins, mouse fibroblasts and their mutant cell lines, REF52 fibroblasts, A7R5 smooth muscle cells, CCL39 fibroblasts and NR6 fibroblasts and combinations thereof. The cells can be isolated from chicken embryos or obtained from American type culture collection (Manassas, Va.).

Measurements on and Mechanical Assembly of a Ring System

Mechanical measurements were carried out using a ring system. After two days of incubation (serum starvation for the final 12-16 hours), the mandrel was removed from the casting well and the tissue model-ring was removed gently from the mandrel. As shown in FIG. 1 the tissue model-ring was looped over the triangular hook connected to an isometric force transducer (Model 52-9545, Harvard Apparatus, South Natick, Mass.) by a fine, flexible gold chain. The ring was also looped over a horizontal bar connected to a sliding element moveable vertically and linearly by a stepper motor (P/N 1-19-3400 24V DC 1.8° step size, Haward Industry, St. Louis, Mo.) controlled by a micro-stepping driver (IM483 Intelligent Motion Systems) to measure stress and dynamic modulus of the sample. The micro-stepping driver was controlled by a personal computer with software which enabled the stepper motor to achieve smooth motion. An analog-to-digital signal converter (CIO-DAS1602/16, Computer Boards, Inc., Mansfield, Mass.) attached to the computer translated the voltage signal from the isometric force transducer to a digital signal for recording on a data recorder. The stepper motor controlled the stretching of the tissue. Force exerted by or on the tissue was transmitted to the force transducer by the gold chain.

The tissue sample was submerged in 50 ml Hepes-buffered DMEM (pH 7.4) in a thermo-regulated organ bath (Harvard Apparatus, South Natick, Mass.) maintained at 37° C. The two horizontal bars over which the ring was looped were initially set to hold the ring at its original contour length (corresponding to the circumference of the mandrel).

Testing of Tissue Model System

Typically, for stiffness measurements, the tissue model is subjected to a sequence of stretch cycles. In each cycle the tissue model is slowly stretched from 0 to 20% over 30 minutes and the tissue model is then returned at the same rate to its original length by actuation of the stepper motor. The resulting increase in contractile force during the first stretch is substantially larger than the contractile force in subsequent stretches (FIG. 2a). For each stretch after the first stretch there is a further small decrease in maximum contractile force, but the decrease becomes negligible after sufficient pre-stretching. The tissue models produced contractile force in response to the activation of fibroblasts by serum. This contractile force was abolished by disrupting the actin cytoskeleton with cytochalasin D (2 µM) (FIG. 2b).

The amplitude of the force response divided by the stretching amplitude corresponded to the dynamic stiffness of the sample subjected to a preselected sinusoidal length change. The dynamic stiffness can be measured at various frequencies and amplitudes. The dynamic stiffness and tension of the FPM were measured at various strain levels by elongating and shortening the sample at a constant rate (10 micrometers/minute) up to 20% strain with superimposed sinusoidal length change (typically, 20 µm amplitude; 0.5% stain, 0.5 Hz frequency) (FIG. 1g). The apparatus is set to change the tissue length with prescribed rate and amplitude.

This determination may be accomplished by separating the cell and matrix contributions within the generated mechanical response profile since the cells, the matrix, and the interactions between the cells and matrix all contribute to the tissue stiffness of a reconstituted tissue model.

As shown in FIG. 3, dynamic stiffness correlates almost linearly to the isometric force (FIG. 3c) while their changes were measured at the original tissue length in response to the FBS stimulation and CD addition (FIGS. 3a, b). Therefore, both the isometric force and the dynamic stiffness are good indicators of the mechanical properties of reconstituted tissues. The application of this method to determine the dose-dependent decrease in the force and stiffness of tissue model caused by the disruption of actin cytoskeleton with two different agents is described below. Data from the examples provide characterization of mechanical properties of connective tissues models, such as fibroblast populated matrices (FPM's) via uniaxial stretch measurements. The tissue model(s) resemble natural tissues in their exponential dependence of stress on strain and linear dependence of stiffness on force at a given strain.

Figure 19:
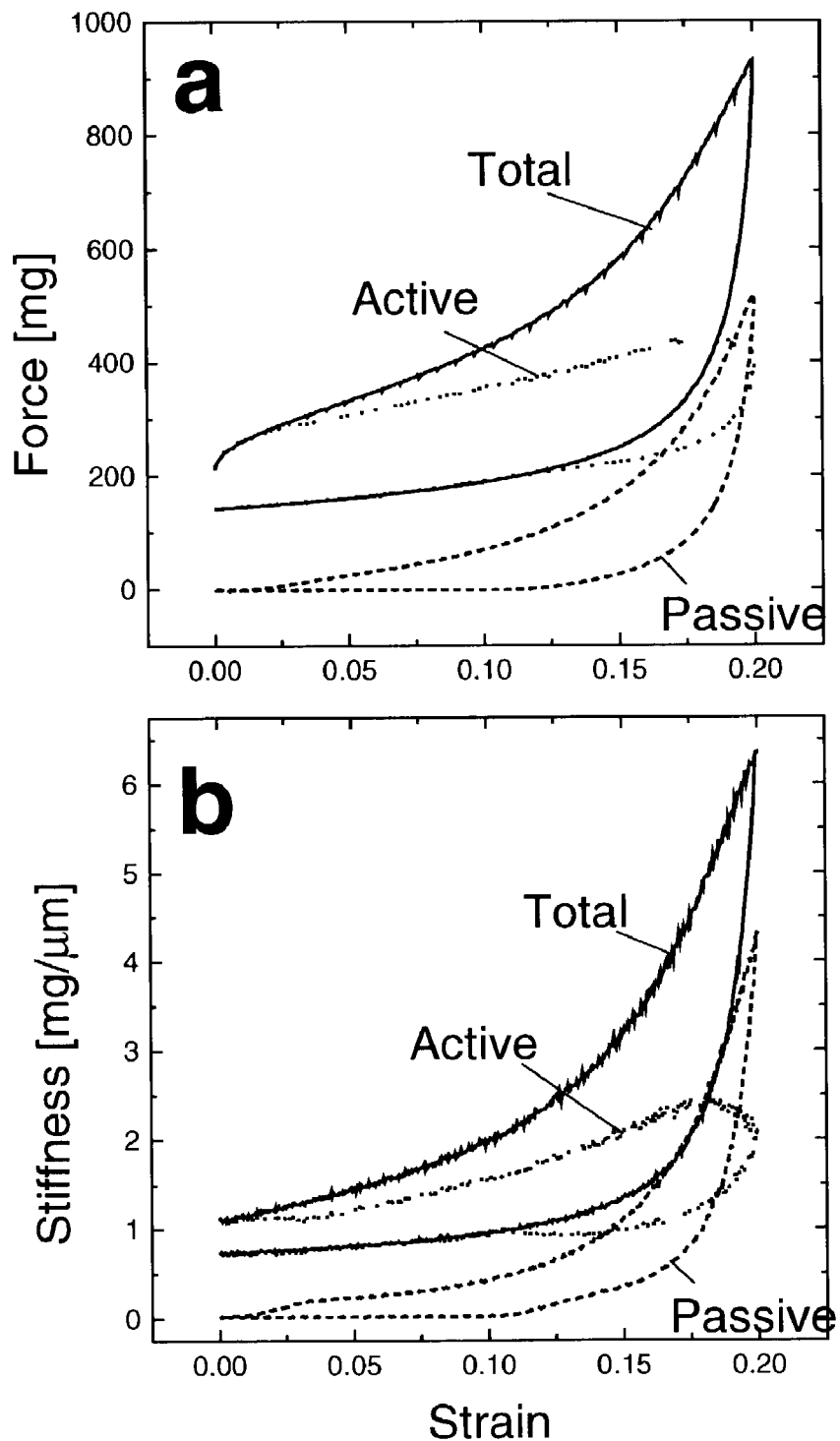

Determination of Contributions of Cells and Matrix to Mechanical Properties of Tissue Model Using a Ring System Determination of cellular contributions and matrix contributions to the mechanical properties of reconstituted tissue models was carried out as it is highly desirable to obtain a more specific profile of the reconstituted cellular response to an activator. Activating cellular contractile forces by calf serum and disrupting F-actin by CD provide active and passive components which respectively emphasize cellular and matrix mechanical contributions. In FIGS. 4,19, the force versus strain (a) and dynamic stiffness vs. strain (b) for a pre-stretched tissue model activated by 20% CS is shown by solid lines labeled "Total". The force and stiffness curves obtained after treatment by 2 µM CD are shown by broken lines labeled "Passive". The difference between the Total and the Passive curves, labeled "Active", is shown by dotted lines. All the curves exhibit hysteresis. The "Active" curve increases approximately linearly with strain; the "Passive" curves increases approximately exponentially. The dynamic stiffness was measured at 0.5 Hz, (b). Note that the dynamic stiffness and the force vary similarly with strain. These measurements were carried out after a single pre-stretch cycle to avoid the large difference between the first and second stretches (see FIG. 2). It has been determined that the "active" and "passive" curves report primarily on the cellular and matrix portions of the tissue model.

The contributions of the cells and matrix are separately (and adequately) assessed. The cellular contributions are eliminated by reducing the stiffness of the cells and effectively disconnecting the cells from the matrix by addition of an effective amount of an actin filament disruptor. This is accomplished by adding CD as a disruptor (for example). CD disrupts actin filament organization within cells as described in detail below. It is therefore possible to determine the effects of activators and inhibitors specifically on cells or on the matrix. This ability to examine separately these two mechanical systems provides further specificity to this method.

CD and Latrunculin-B (LA-B) are two agents that disrupt the actin filament cytoskeleton and therefore both prevent the development of contractile force and weaken cellular mechanical properties. The response of a tissue model to CD and LA-B including dose-dependent mechanical properties were determined.

As used herein the term "isometric force" includes the force change without substantial change in the tissue length or tissue physical dimensions.

The isometric force and the dynamic stiffness of two day-old tissue models, which have been serum starved for 16 hours prior to the experiment, were measured over a range of CD concentrations. The measurements were carried out serially on each tissue model, beginning with the lowest concentration of CD. For each tissue model, CD was added and force and stiffness were measured and then the CD concentration was increased for the next measurement (FIGS. 4A, B). The CD was dissolved in DMSO. The total amount of DMSO added to the organ baths containing the tissue model was less than 0.1% of the total volume of the DMEM. This quantity of DMSO had no significant effect on the force and stiffness of FPM's. The data shown were averaged over quadruplicated samples, and the same experiment was repeated at least twice. The force and dynamic stiffness were significantly decreased at a CD concentration as low as 2 nM. At this concentration, no effect was observed by confocal microscopy on the actin cytoskeletons stained with Rhodamine phalloidin in monolayer cell cultures. Both force and dynamic stiffness continued to decrease as the CD concentration increased up to 2 µM. At this concentration, the force was reduced almost to zero and the stiffness had nearly reached its minimum value. For CD concentrations higher than 2 µM, the stiffness did not significantly diminish further (data not shown). The concentration of CD needed to reduce the force and dynamic stiffness by 50% was approximately 0.25 µM.

Measurements of the effects of LA-B on the mechanics of tissue models demonstrated differences between the mechanism of action of LA-B and the mode of action of CD on the actin cytoskeleton. Incremental additions of LA-B and mechanical measurements on tissue models were carried out serially as in the studies of CD. The data were averaged for at least three samples, and the same test was repeated at least twice. The concentration of LA-B needed to produce a significant effect on the tension and the stiffness of FPM's was much higher than that required of CD (FIGS. 4D, E).

Force and stiffness had a sigmoidal dependence on LA-B concentration. The estimated half maximum concentrations for reducing the force and stiffness were 53 nM and 68 nM, respectively. The LA-B-dependent decrease of tension and stiffness was confined to a single decade of LA-B concentration, whereas the response to CD ranged over almost three decades. This strongly suggests that CD and LA-B operate by different mechanisms to disrupt the actin cytoskeleton. Small differences in the values of force at the high concentration limits of CD and LA-B (FIG. 4) were observed.

For a viscoelastic system the dynamic stiffness depends on both the elastic and viscous resistance to stretching. The viscous contribution can be measured by the phase angle, δ, between force and strain.

In these tests the change of phase angle, δ, due to disruption of the actin cytoskeleton was small (data not shown). Hence, in this system CD and LA-B had a relatively minor effect on the viscosity of the tissues. Therefore, it is reasonable to suppose that the viscous contribution of the cells to tissue model force and stiffness was also minor. These measurements illustrate how force and stiffness measurements rapidly and sensitively indicate the effects of these "inhibitors" via their effects on the actin filament system.

Figure 10:
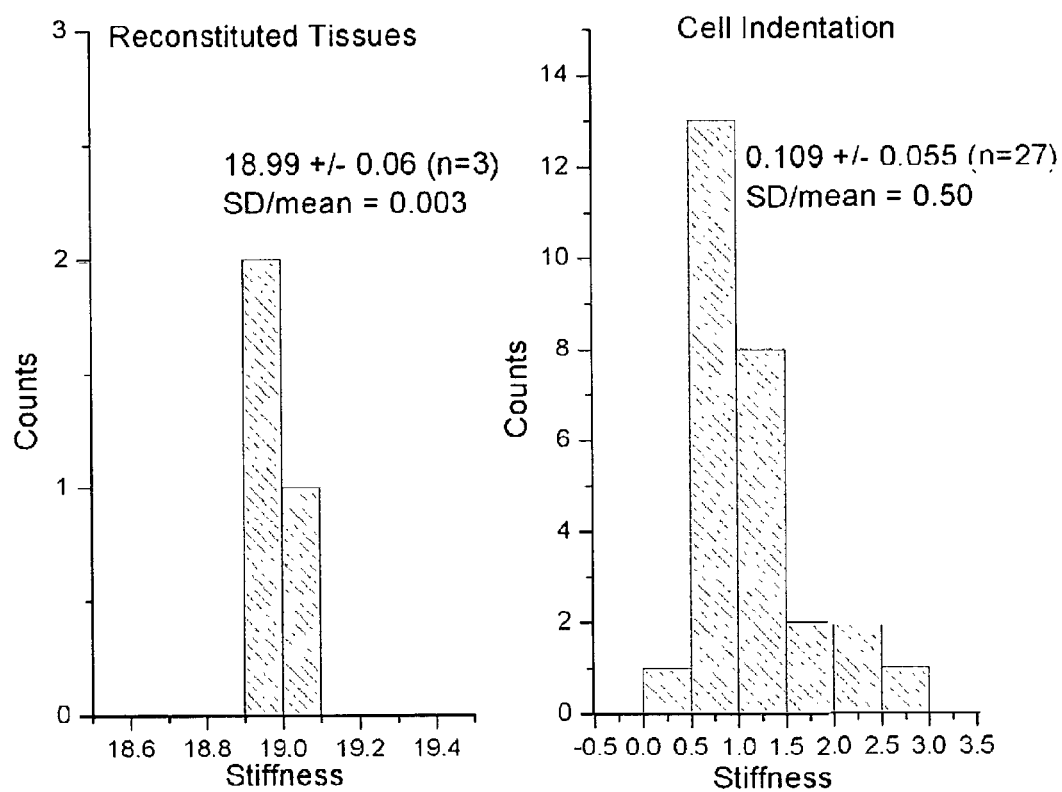
FIG. 10 is a comparison of data variance for measurements of tissue stiffness using the reconstituted tissue ring method (left side) and a single cell indentation method (right side).

In an embodiment of this invention using an indentation (indention) procedure in a multi-well plate system, mechanical response parameters are determined that are averaged over at least 100,000 cells. Measurements on reconstituted tissue models obtained using this system were compared with those obtained by indentation of individual cells. (Pertersen et al. 1982, Zahalak et al. 1990). For example, stiffness of the reconstituted tissues was measured with good statistical significance with ten-fold fewer measurement points using the ring system than are required for cell indentation measurements on individual cells (FIG. 10).

Many signal transduction pathways contribute to the mechanical properties of reconstituted tissues by regulating contractile force, the organization of the cytoskeleton, and the integrity of the extracellular matrix. Therefore, a wide range of intracellular and extracellular target molecules can be assayed by determining their effects on the mechanical properties of reconstituted tissues using this invention.

The cells in the reconstituted tissue models of this invention are in an environment that resembles their condition in natural tissues and organs. Therefore, results of the assays using this method yield results similar to those obtained using animal models. Some of the animal testing can be replaced by using tissue models. For example, some tests of agents acting on skin can be conducted using artificial living tissues.

In an embodiment, the aforedescribed methods can also be used to detect the effects of toxic materials on the mechanical properties of reconstituted tissues. For example, the inventors discovered that a 10% solution of ethanol reduces force and stiffness of tissue models significantly. The inventors observed that infection of cells in tissue models by viruses can diminish force and stiffness. Therefore, the aforedescribed method can be utilized to determine the toxicological effects of substances and biological materials.

Cardiac Tissue Models

The tissue models made using cardiac myocytes isolated form chicken embryos become contractile spontaneously. Chicken embryo extracts (CEE, Life Technologies, Rockville, Md.) have been known to be required to form spontaneously contracting artificial cardiac tissues (FASEB J 1997 July;11(8):683-94, FASEB J 2000 April;14(5):669-79). Media conditioned by cardiac fibroblasts can replace the CEE. The conditioned medium (CM) was produced by incubating a confluent monolayer of cardiac fibroblasts in 100 mm dish preincubated with DMEM supplemented with 10% FBS for 2 days. The medium is changed to DMEM containing no serum and is incubated for 24 to 48 hours to make the CM. The cardiac tissue models cultured with the CM supplemented with 10% FBS start spontaneously contracting in 4 to 5 days without adding any CEE. The cardiac myocytes grown in the tissue models spread much better (FIG. 5a) than those cultured in DMEM containing only 10% FBS (FIG. 5b). A similar difference is observed for cells growing on tissue culture dishes. The cardiac myocytes cultured in the CM (FIG. 5c) spread much better and cover larger areas than those cultured in DMEM supplemented with only 10% FBS (FIG. 5d). This suggests that factors secreted by the fibroblasts promote cardiac myocytes spreading and spontaneous contraction. Conditioning of medium by which cardiac myocytes are induced to spread and contract spontaneously is also accomplished by coculturing cardiac fibroblasts as a monolayer at the bottom of the tissue culture dishes incubating cardiac tissue models. The conditioning of medium promoting spontaneous contraction of the cardiac tissue models is also accomplished by coculturing connective tissue models containing cardiac fibroblasts. The fibroblasts can also be mixed with myocytes to form cardiac tissue models. This induces strong contraction in 4 to 5 days yet it also stops spontaneous contraction as early us 7 to 8 days of the culture. See the description of the various conditions in supplemental table in FIG. 5.

Cardiac Tissue With Mouse Cells

Figure 6:
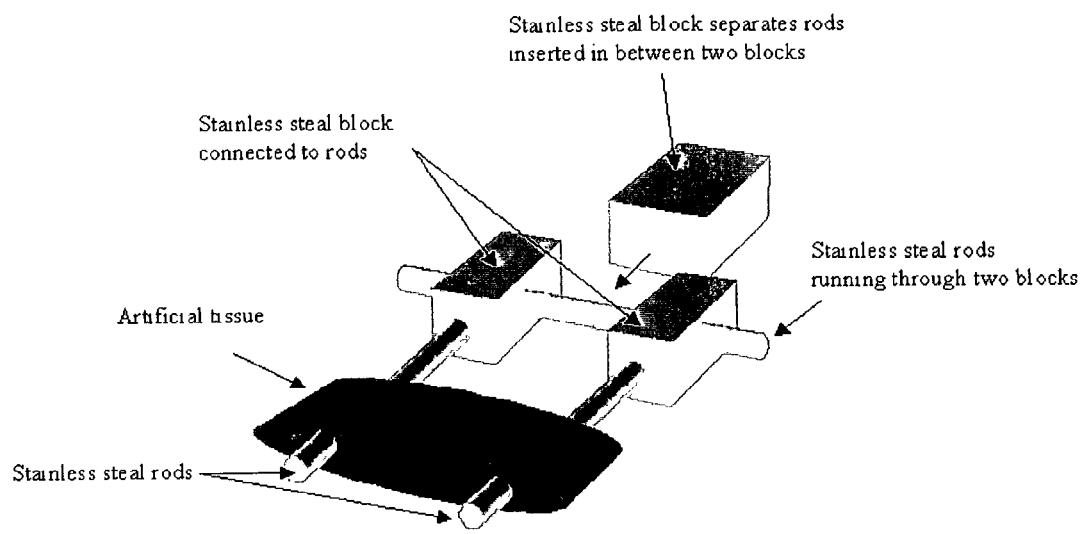
FIG. 6 is a stainless steel spacer used to culture model tissues after removal from the molds shown in FIGS. 1c and 1e.

Embryonic hearts are removed form stage E17-E19 mouse embryos. Cardiac myocytes are isolated by several collagenase (167 µg/ml) digestions after 15 min. trypsin (0.25%) treatment at 37° C. Isolated cells from the hearts are cultured on tissue culture grade plastic dishes for 1 hour to remove nonmuscle cells by the rate of adhesion to the tissue culture grade dishes (nonmuscle cells adhere much faster than the muscle cells). Non adherent cells are removed with medium and sedimented with low speed centrifugation for 15 min. For 1 ml of artificial tissue, 1 million myocytes were mixed with 0.75 mg of rat tail collagen kept in acetic acid (0.02 N), which is neutralized by adding an appropriate amount of NaOH (0.1N), and 0.25 mg of fibrinogen kept in phosphate buffered saline. A higher concentration (more than 1×) of tissue culture medium (DMEM) is added to the sample solution to maintain a normal final concentration of the medium. One µl of thrombin (1 unit/ml) was also added to the solution to initiate fibrin formation. The fibrin converted from fibrinogen polymerizes with collagen to form a stronger gel, which facilitates handling the sample. The 0.5 ml of sample solution was poured into a mold described previously and incubated in the tissue culture incubator (5% $CO_2$ at 37° C.) for 30 min. The gel is removed from the mold and cultured with the spacer—two stainless steal bars (~1 mm in diameter) separated by a stainless steel block (FIG. 6). After incubation of 5-7 days embryonic myocytes spread into the collagen/fibrin gels and spontaneously twitch. The cells make contact with one another and start twitching synchronously.

Figure 7:
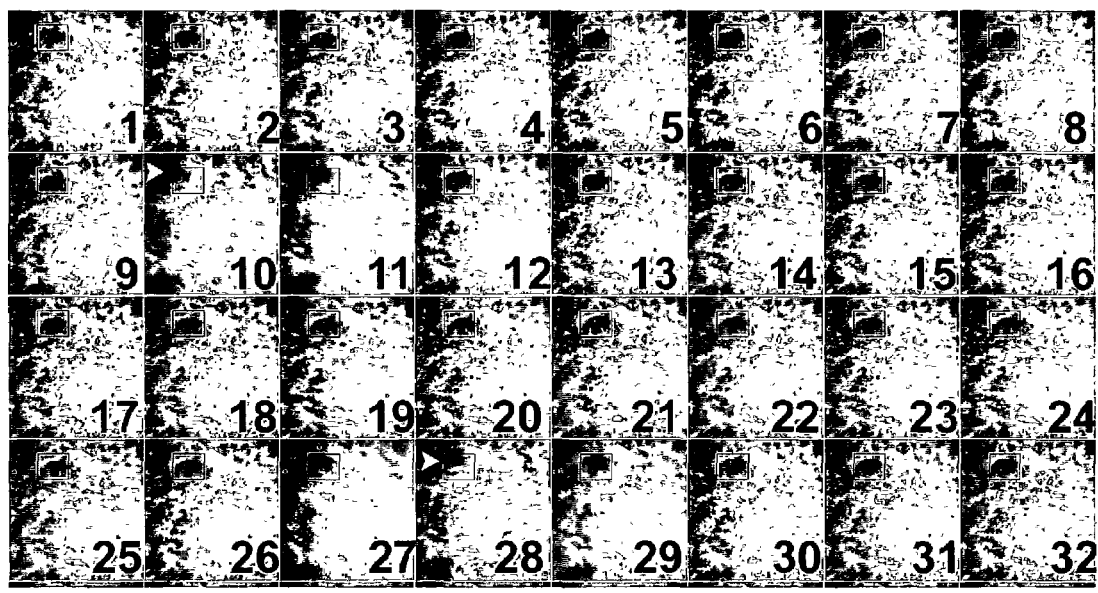
FIG. 7 shows a time sequence of images (1 through 32 with a 200-msec. interval) capturing spontaneous contraction of cardiac tissue models made using cells from embryonic mouse hearts.

A sequence of images captured the mouse embryo cardiac tissues was shown in FIG. 7. A dark feature within the image is enclosed by a rectangular frame. The frame in each image is stationary. Displacement of the feature away from the frame periodically indicated by white arrows at image 10 and 18 indicates twitching of the sample by the cardiac myocytes (FIG. 7).

In vitro tissue models made using mouse cells and mimicking the mechanical properties of mouse cardiac tissues are useful test system for evaluating the effects of pharmaceutical candidates. Well established methods of for knocking out specific genes in mice has created an enormous number of mutant mice lacking specific molecules by which cardiac functions are regulated. For instance, studies using a mouse lacking type 1 NO synthase (Circulation June 25, 2002;105(25):3011-6), Connexin43 (Development 2002 April;129(8):2031-42), and familial hypertrophic cardiomyopathy linked to myosin binding protein-C (Circ Res March 22, 2002;90(5):594-601) are just few examples published in 2002. Model cardiac tissue can be made using cells from a knockout mouse to study the role of a specific protein molecule in cardiac development and function. Many knockout mice do not survive after birth or even beyond a defined embryonic stage. Therefore, functional studies of the heart of these knockout mice are limited. Since cells isolated from embryonic or neonatal mice can be used to make functional tissues, the system can be used to study functions of molecules, which are inaccessible using intact tissue or whole animals. The study of knockout mice is useful for studying the efficacy of gene therapies in vitro.

Miniaturization of Tissue Models

Figure 8:
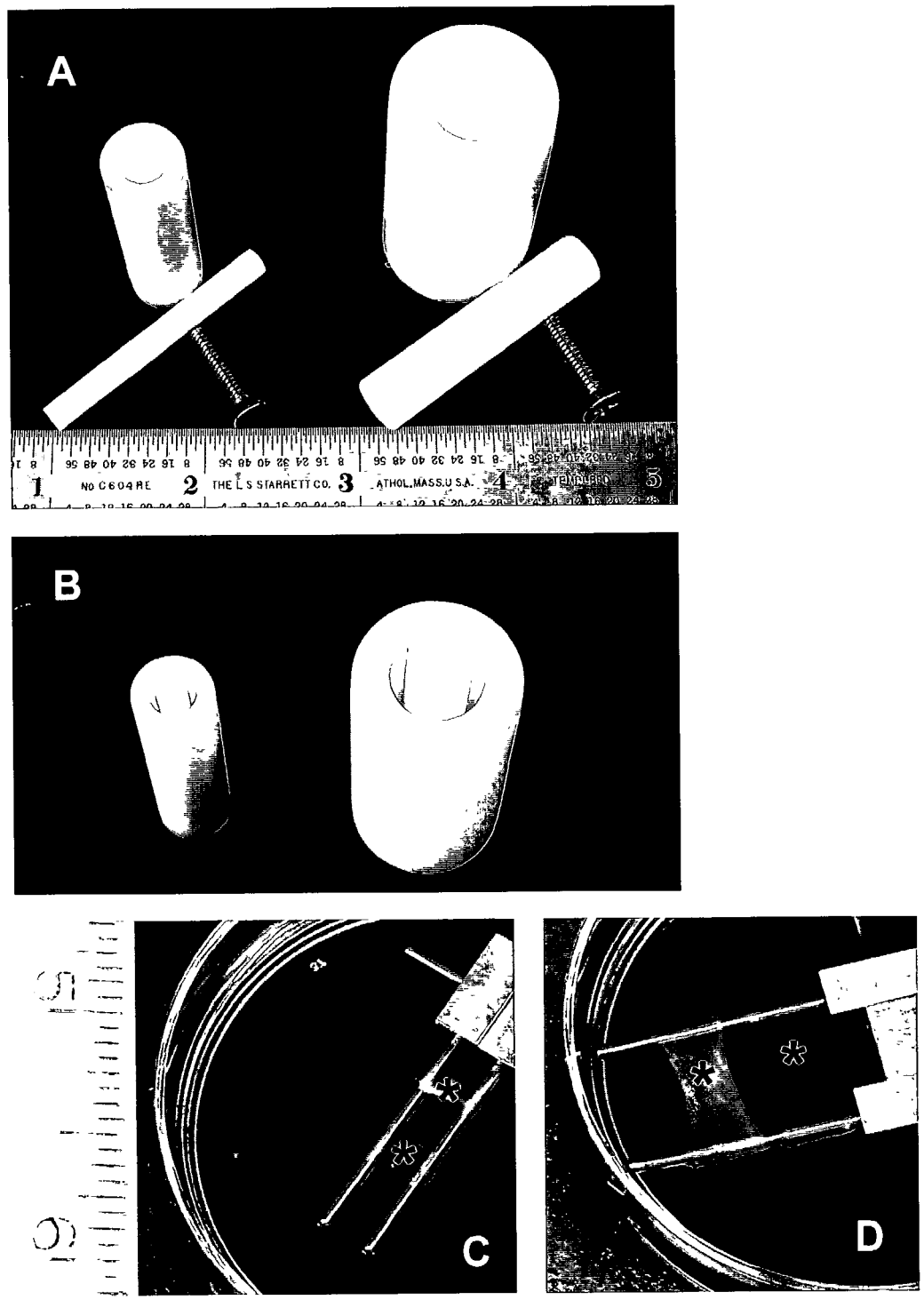
FIG. 8 shows photo images of regular and small size tissue molds and the tissue models.

The samples are miniaturized by using a smaller mold (right in FIGS. 8a, b) instead of the one used ordinarily (left in FIGS. 8a, b). The sample sizes are determined by the diameters of the mandrels and inner diameters of the wells. The molds before (A) and after (B) assembling the parts are shown in the FIG. 8 . The mandrel diameters of small and regular size molds are 3/16 and 3/8 inches, respectively. The inner diameters of the small and regular size wells are 9/32 and 17/32 inches, respectively. By using the smaller mold, the size of tissues are decreased 5-fold in volume (1 ml to 0.2 ml) (* indicates the tissue samples in FIGS. 8c, d). The miniaturization of the tissue model allows us to do tests similar to those described in FIGS. 2, 3, 4, 15, 16, 17, 18, 19, 20, 21, 23 using regular size samples but in much smaller organ baths using less medium consuming a fraction of the chemicals used in the tests. At least a 5-fold reduction, which is equal to the reduction of sample volume, can be achieved.

Figure 9:
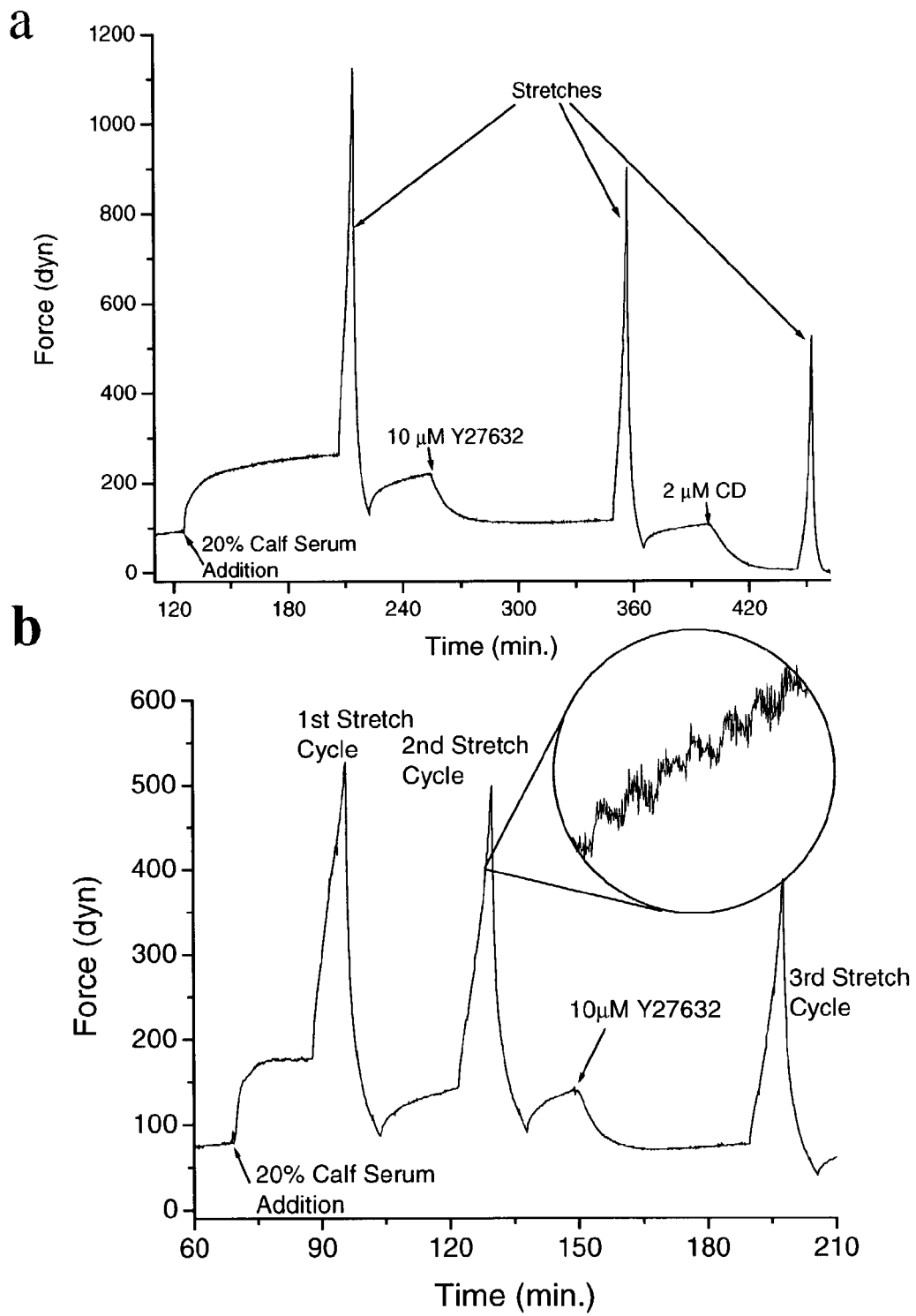
FIG. 9 is a comparison of force traces observed using small and regular size cardiac tissue models made using these molds. The change of force with time shown in FIG. 9a is observed using a cardiac tissue model made with the regular size mold. The change of force with time in response to stretch and treatment with Y27632, an inhibitor of the activation of myosin activation by Rho kinase, is shown in FIG. 9b. The insert of FIG. 9b shows an enlarged plot of force and time during the sample stretch spontaneously contracting.

To demonstrate and prove this concept, the mechanical responses of the cardiac tissue models to the treatment of serum and Y27632 are observed (FIG. 9). The tissue models are made using regular size mold with chicken cardiac cells (9a). They typically look like the tissue models (indicated by *) shown in FIG. 8d. FIG. 9b also shows the similar trace of force obtained with miniaturized tissues, which look like the ones in FIG. 8c. Both sizes of tissues increase force in response to 20% (v/v) calf serum and forces are decreased by Y27632 treatments. Differences in magnitudes of changes in response to these chemicals using different sizes of tissue models are not greater than 2 fold. This demonstrates that the miniaturized system hasve a large enough range of signal to detect changes induced by pharmaceutical candidates. The miniaturized system also shows force-response curve to mechanical stretches similar to that of the normal-sized tissues. Miniaturized samples made using chick cardiac cells show twitch forces. Therefore this system can be used to test the effects of pharmaceutical candidates treating cardiac dysfunctions (Insert in FIG. 9b)

Tissue Model Measurements in Multi-Cell Indentation System (Using a Multi-Well Plate)

Fabrication and measurement of miniaturized reconstituted tissue specimens were carried out using membranes and strips of reconstituted tissues in wells of a 96-well plate system.

Mechanical Assembly of a Multi-Well Plate System

A triangular frame made of stainless steel wire 1 mm in diameter was employed as a scaffold on which the reconstituted tissue formed. The wells are slightly tapered toward the bottom and the frame is securely positioned 1 mm above the bottom of the well (FIG. 11a). The non-polymerized solution of collagen containing cells and appropriate cell culture media as described above was poured into the wells filling the wells to a level 3 mm above the bottom (FIG. 11b). The 96-well plate was incubated at 37° C. with 5% $CO_2$. During the incubation, cells compressed collagen matrices by squeezing liquid out from the porous collagen matrix. Without the wire frame, the reconstituted tissue contracted into a small sphere floating in the tissue culture medium. It was discovered that by utilizing different shapes of wire frames the collagen matrix was compressed into shapes corresponding to shapes of the frames. Illustratively, a triangular wire frame made a membrane spanning among the three edges is shown in FIG. 11a. Other wire frame shapes, such as one shown in FIG. 11b, produced tissue strips with different width. A porous support material such as Velcro fastener was not required to facilitate tissue adhesion even to the non-porous stainless steel surfaces of a wire. The collagen was compressed to a greater extent at the outer portion of the membrane or strip. Therefore, this outer portion of the membrane can withstand stress produced by the cells and prevented it from ripping the membrane off the wire frame.

Measurement Of Force, Tissue Stiffness and Hysteresis of Membranes or Strips Using an Indentation Method (in a Well Plate System)

To assess the response of the tissue model samples to test agents, the resistance of the tissue samples to stretch is measured by a probe coupled to a force transducer. The stiffness of the tissue is related to the force required to move the probe by a specified amount once the probe contacts the tissue. The probe, consisting of a vertical glass tube whose tip has been smoothed by fire polishing, is attached to an isometric force transducer (described above). The diameter of the probe is about 2 to 3 mm and the shape of its tip can be flat or hemispherical. The probe is firmly attached to a beam and the beam attached to the force transducer by glue or wax (FIG. 11a). The force transducer is attached to a stationary frame. The 96-well plates are placed on a stage that moves vertically. The stage constructed for demonstration of the method uses a micrometer driven by a computer-controlled stepper motor to raise or lower the stage at prescribed incremental rates. In this implementation the range of stage motion is 0 mm to 15 mm at a maximum velocity of 500 µm/sec. The same apparatus has been used for large-scale tissue mechanical measurements. A detailed description is provided below in the following section on force measurements.

Sample Preparation of Tissue System for Using the Indentation Method (in a Well Plate System)

During the tissue formation and continued culturing of tissue models, the samples were kept in a 5% $CO_2$ incubator at 37° C. with bicarbonate buffered DMEM supplemented with 10% FBS, penicillin, and streptomycin. For force measurements the medium was changed to 150 µl of HEPES-buffered DMEM without serum. The temperature of the medium was kept at 37° C. by placing the wells on a heated plate connected to a temperature-controlled circulation bath.

Measurements Using Tissue Indentation Method (in a Well Plate System)

The stage is raised until the probe tip touches the membrane or strip of reconstituted tissue. Contact of the tip with the sample is detected by a sudden increase in the force registered by the isometric force transducer. The stage is then lowered by 5 µm, i.e. tip is withdrawn from contact with the sample. Then the stage is moved vertically according to a saw-tooth wave-form at 3.3 µm/sec with 100 µm amplitude. During this trajectory the tip comes in contact with the tissue specimen and stretches it as the force is continually recorded by a data recorder. The velocity can be varied to optimize the sensitivity of measurements and to measure the viscosity of the sample.

After the peak force reaches its steady level the sample is stimulated with 20% Fetal Bovine Serum (FBS) (arrow a in FIG. 12a). This amount of FBS activates fibroblast non-muscle myosin producing a contractile force that stiffens the reconstituted tissues. About 10 min. after the FBS addition, there is a ~25% increase in the peak force of subsequent indentations (FIG. 12a). Nearly 15 min. after the addition to the medium of 40 nM CD (arrow b), the peak force from subsequent indentations has decreased ~40% from its initial level (FIG. 12). A further reduction of peak force was recorded 20 min. after addition of 2 µM CD.

A plot of force versus indentation depth during the membrane stretching follows a different path from that seen as the stress is relaxed by retraction of the probe from the sample, establishing a hysteresis area between the two curves. Upon additions of FBS or CD, changes in the hysteresis areas are compared in FIG. 12(b). Percent changes in the peak force and area of hysteresis during the experiment shown above are compared in FIG. 13. The area of hysteresis changes to a greater extent upon stiffening due to myosin activation and CD addition. Therefore, the area of hysteresis is a more sensitive parameter than the peak force for monitoring the changes in mechanical properties of the sample.

Test Using Physiological Activators to Activate Force Response Without Stretching Ring samples made using a rat embryo fibroblast derived cell line (REF52) were prepared as described previously herein. The length of the tissue was maintained at a constant level during the test. Each of the drugs indicated in FIGS. 1020 15 was added to a single tissue ring. Thrombin, vasopressin, lysophosphatidic acid (LPA), bradykinin, and endothelin contacted the ring to produce different forces that develop in different response times (FIGS. 15). Norepinephrine and phenylephrine relaxed the contractility of the ring, and therefore norepinephrine and phenylephrine reduced the initial base line force of tissue indicated at the beginning of each test (FIG. 15) (reagents used are obtain from Sigma, St. Louis, Mo.).

Profiles of contractile response to different agonists applied to ring samples were made using chicken embryo cardiac fibroblasts (CECFs) and rat adult cardiac fibroblasts (RACFs) and are shown in FIG. 16(*a*), 16(*b*), 16(*c*), 16(*d*) and FIG. 16(*e*), 16(*f*), 16(*g*), 16(*h*), respectively.

RACFs responded to vasopressin (FIG. 1*f*) and angiotensin II (FIG. 16*g*) whereas CECFs did not response to vasopressin (FIG. 16 a) and angiotensin II (FIG. 16*c*). CECFs did not respond to any dose of EGF stimulation (FIG. 16*d*). Endothelin stimulation contracted rings made using both CECFs (FIG. 16*b*) and RACFs (FIG. 16*h*). Time dependent force profiles after addition of FBS (20% v/v) were different depending on the pretreatment by different agonists.

For example, FBS addition resulted in a double peak of force after EGF pretreatment (FIG. 16*d*). The force level is sustained after FBS addition to a system previously treated with angiotensin II. Yet the force level started to decrease from its FBS stimulated peak level after treatment with vasopressin and endothelin (FIG. 16*a*, b).

This invention is useful for managing the profiles not only of single compounds but also of combinations of multiple compounds applied at the same time or at different times. Managing profiles of combinations of multiple pharmaceuticals is useful both for screening purposes and also to reveal unexpected consequences caused by combinations of multiple pharmaceuticals.

The myosin ATPase inhibitor BDM reduces in a dose dependent manner (FIG. 17) the fully activated contractile force produced by prior addition of 20% FBS.

The contractile force developed by the ring sample during matrix remodeling and compression can be measured by connecting the ring to the force measuring apparatus as described above within about 1-2 hours after collagen gelation. The cells begin to exert a force on the matrix after this time. Then the increase of force during tissue development (remodeling and compression) is observed over time.

A profile of force measured during the ring tissue development is shown in FIG. 18(*a*). Maximum force is typically reached within 15 to 20 hours. This process was also disrupted by several inhibitors as illustrated in FIG. 18(*b*), (*c*), (*d*). The tTyrosine kinase inhibitor, herbimycin A (FIG. 18*b*) reduces the maximum force as does the microtubule disrupting reagent nocodazole (FIG. 18*c*). Cytochalasin D (2 µM) completely abolished the development of force from the beginning of the test.

This invention has broad utility including using this invention for high-throughput pharmaceutical drug screening and treatment testing. For example, reconstituted tissues in the form of membranes or strips could be mass-produced to supply 96 uniform samples, one in each well of a 96-well plate. Simultaneous force measurements could also be achieved by using 4 or more force transducers (FIG. 11). The 96-well plate is placed on an x-y stage that positions the samples at the correct locations for the indentation measurements. Probes attached to force transducers move vertically to indent the samples (FIG. 11*a*). A single force transducer can be used to indent several samples within a short period of time by repositioning the 96-well plate using the x-y stage. The addition of chemical compounds and small peptides to the sample and movement of the stage and force transducers can all be automated and controlled by a personal computer. The computer also stores and analyzes the data in a database.

Genes and proteins can be delivered to the cells as agents within the reconstituted tissues using various techniques available herein.

The number of wells per plate may vary in accordance with the size of the system being utilized in an indentation (indention) setup. Typically the number of wells per plate is from about 2 to about 1000 or more preferably from about 50 to about 500 wells per plate.

Applications of this method in addition to drug screening include testing procedures for delivering genes to cells as agents. The reconstituted tissue samples can be made using cells lacking genes that contribute to cell and tissue mechanical properties. Hence, the recovery of normal tissue mechanical characteristics provides an assay for the effective delivery of the gene.

The ring tissue model system can detect the effect of a genetic deletion on the ability of cells to generate force both while compressing and remodeling the collagen matrix and while responding to calf serum. Cells interact with and adhere to diverse ECM constituents through specific heterodimeric receptors called integrins on their surface membranes. Each integrin is composed of one α and one β subunit. The integrins that mediate binding to collagen are $\alpha_1\beta_1$ and $\alpha_1\beta_1$. NMuMG, is an immortalized but nonmalignant mouse mammary epithelial cell line that does not express $\alpha_1$ and $\alpha_2$ integrin. Hence, these cells interact weakly if at all with collagen matrices and therefore cannot transmit force to the ECM to generate and to maintain tissue stiffness. FIG. 20 demonstrates that cells without $\alpha_1$ and $\alpha_2$ integrin could not develop baseline force during tissue development nor could it respond to calf serum (CS) by increasing force (FIG. 20*a, b*). Also shown is the rescue of these two functions by re-expressing normal $\alpha_2$. The cells containing the $\alpha_2$ gene normally adhered to and compressed the matrix and responded to CS (FIG. 20*a, b*). This example illustrates the useful application of the invention to generate and to manage the mechanical response profiles that report on gene expression. Hence, the invention is useful to manage the mechanical response profiles as indicators of genotype and of the results of gene therapy, such as the efficiency of different methods of gene delivery.

Reconstituted tissue models can be used to assess quantitatively and rapidly the effects of many different classes of potential pharmaceuticals, toxins, and pathogens as agent(s) on the mechanical properties of cells and matrix. These mechanical properties provide general indicators of the overall organization of cellular mechanical systems, especially the cytoskeleton, of the operation of signal transduction pathways, and of the organization imposed on the matrix by the cells during tissue development. Therefore they provide potential applications in a wide range of disease areas.

Example of Potential Pharmaceutical Candidate Testing

We demonstrated dose dependent stress relaxation of the tension in reconstituted tissues using Y27632, which has promise for the treatment of hypertension.

The connective tissue models made using NIH 3T3 cells were treated with different amounts of the candidate pharmaceutical, Y27632. Rho kinase specific inhibitor, Y27632 has been tested for reducing tension of smooth muscle strips such as rabbit aortic rings (Nature 239 (1997) 990-993). It is one of the promising drug candidates treating hypertension in the future. Depending on the agonists used to stimulate the tissue contraction, the degree of reduction in tension is different (FIG. 21). Y27632 reduces the tension of connective tissue models in a similar dose-dependent fashion (FIG. 21). This demonstrates the utility of technology in screening the pharmaceutical candidates.

The collagens in tissues are degraded and recycled by the family of enzymes called matrix metalloproteases (MMPs), which are secreted as latent proenzymes. The enzymes become active through proteolytic cleavage of their amino-terminal domain, and their activities depend on the presence of $Zn^{++}$ and $Ca^{++}$. MMP-2 activity is known to play a role in tumor cell invasion. The presence of MMPs both in pro- and active-forms is detected by a technique commonly known as zymography. Chicken cardiac fibroblasts are cultured for 2 days with DMEMs supplemented with none or 0.5% fetal bovine serum. The MMP-2 and 9 are secreted by the cells into the medium and their presence is detected by the zymograph. In FIG. 22 the control lanes 11 through 15 are loaded with purified proenzymes of MMP-2 and 9. This shows that at least 0.5 ng of enzyme (lane 11) can be detected using the assay (FIG. 22). The smaller active enzyme runs ahead of proenzymes and a band of active enzyme appears at lower positioned of than the band of inactive MMP-2. Medium conditioned by the cells growing on tissue culture dishes with no coating, or with fibronectin, or collagen coating do not show any bands of active enzymes. The medium conditioned by the cells grown in 3 D collagen matrix, i.e., tissue model, shows a band of active MMP-2 (lanes 9 and 10). This indicates that the cells on 2D substrata secrete inactive enzymes into the medium but they are not activated. The enzymes never get activated unless the cells are grown in 3 dimensional matrices. Therefore, the investigation of MMP activities affecting extracellular matrix degradation such as during tumor invasion requires a model system such as the tissue models in which the cells are growing in 3 dimensional matrices. This is especially important for discovering inhibitors of MMPs.

The effects of the general inhibitor of MMPs, GM6001 (Biomol Research Laboratories Inc. Plymouth Meeting, Pa.) (N-[(2R)-2-(Hydroxamidocarbonylmethyl)-4-methylpentanoyl]-L-tryptophan methylamide) on the mechanical properties of artificial tissues have been investigated. The tissue models made using cardiac fibroblasts are incubated with 50 µM GM6001 for 6 days. The tissue culture medium is replenished every other day with fresh medium containing GM6001. The tissue model rings are subjected to mechanical tests as described above. The GM6001 treated samples (dash lines in FIG. 23) show significant reduction in mechanical properties of the samples compared to those of controls (solid lines). Although the Ki values of GM6001 for different MMPs are around nmol/l, the effects of GM6001 in animals can be observed only with a high concentration of the inhibitor (sub mmol/l) (Circ Res 1996 January;78(1):38-43). This suggests that the Ki value measured in a purified system does not directly correlate to the inhibitory effect of drug in living test subjects such as animals or tissue models. MMP inhibitors affecting the mechanical properties of various tissue models can be discovered efficiently using the high throughput system.

This invention has many additional utilities. For guiding treatment cardiac diseases, reconstituted tissue models assembled from cardiac myocytes and/or cardiac fibroblasts can be used to test the effects of candidate pharmaceuticals on cell and matrix remodeling processes that result from pressure overload and on tissue restructuring that occurs in response to trauma or infarction. This invention can be employed to guide treatment of dental connective tissue diseases-, cancer metastasis- (contraction, traction force in cell motility), diabetes (stiffening of connective tissues and skin by collagen cross linking), pulmonary diseases such as emphysema, chronic inflammation (elastase secreted from neutrophils), muscular dystrophy and aging skin.

This invention also comprises a method of managing a library of pharmaceuticals. This method comprises obtaining a profile of mechanical response to the contact of an activator with a tissue model system wherein a tissue model has been contacted with the pharmaceutical, storing that profile in a database, storing at least one additional profile of another pharmaceutical in a tissue model system in that database, setting up a means for comparing with another profile, one profile, comparing the profile of the first pharmaceutical with the profile of a second pharmaceutical based on a pre-established or ordered standard of comparison. The pharmaceuticals are ranked in an order of activity with respect to mechanical effect on the tissue model system based on their respective profile.

Possible Parameters to Analyze Curves

The force response initiated by an agonist addition plotted over time can be presented using several parameters to describe the shape of the curve. The $F_0$ and $\Delta Fmax$ represent initial the force level before the agonist addition and the maximum change in force respectively. The $\Delta Tmax$ represent the time to complete the change in force level. The time derivative of the force curve represents the velocity of the change of force with time. The maximum value of dF/dt, Vmax, represents a maximum slope in the force curve. These parameters are useful to make a profile of pharmaceutical candidates in terms of the changes the tension level of the artificial tissues (FIG. 24)

In an embodiment, the profile of a candidate pharmaceutical is compared to the profile of a known pharmaceutical and a ranking or rating is made based on that comparison to provide information and guidance as to whether the candidate pharmaceutical would likely be an effective pharmaceutical.

Further, if desired, a test is carried out in accordance with this invention, wherein the candidate pharmaceutical is evaluated against a particular cell system which is known to be involved in a particular disease. In this embodiment, the cellular response thereto using the system of this invention is employed to provide an indication of the probable activity of the candidate pharmaceutical to a particular cell type. In a further embodiment, the pharmaceutical is evaluated in a tissue model system and compared to the evaluation of a pharmaceutical known to be useful in treating a particular disease.

In a further embodiment, the profile of the known pharmaceutical is one which is known to provide effective treatment against a known disease. In this embodiment a comparison is thus made wherein the pharmaceutical is evaluated against cells which are known to be involved in a particular disease. This embodiment is useful in determining whether a pharmaceutical is potentially useful in the treatment of heart disease or hypertension or aging for example.

Hypertension is caused by elevated contractility and stiffness of blood vessels. Drugs for hypertension can be identified using this invention. These drugs can be used to lower the blood pressure of the animal or tension and stiffness of isolated blood vessels from the animal. This invention uses artificial tissues mimicking blood vessels using tissue cultured cells and extracellular matrices, the method herein can replace animal models or explanted tissues.

Artificial tissues are made to mimic specific biological functions or different types of organs and tissues including skin, muscle, heart, and blood vessels or to mimic more complex tissues by co-culturing different cell types in a single artificial tissue. Since the mechanical properties of the tissues are correlated to their structural integrity by using this invention, they are important parameters to indicate biological functions of tissues and organs.

In addition, this invention can be used to screen compounds at high speed based on their biological activities affecting the mechanical properties of the artificial tissues. For example, artificial tissues are made in small sizes to fit in one of the wells (4 mm in diameter and 6 mm in height) in a 96-well plate. The significantly miniaturized sample preparation reduces the amount of compounds used in each testing at least by 90% compared to known methods, such as using aortic rings. Since animal tissues are surgically isolated from animals, their sizes and responses to the drugs are not necessarily reproducible.

Toxicity of pharmaceutical compounds can be determined using the method of this invention. For example a different dose of ethanol causes a decrease in the level of baseline force maintained by the viable cells.

In another aspect, the biochemical properties of cells and matrices comprising model tissue are measured optically using, for example, fluorescence markers.

Using the invention, one can create a new library of profiles of pharmaceuticals based on their effect on the mechanical properties of live artificial tissues. The number of active compounds in the library created by the instant invention using the indentation system is most likely to be less than that in the library created by a prior art test tube based screening system. Compounds selected in chemical screening procedures may include many that elicit no physiological response.

The chemical compounds screened by the artificial tissues based system will have a higher chance of having similar effects on the mechanical properties of real tissues and organs in animals and humans. Therefore, the use of animal models for an optimization stage of drug screening can be significantly reduced using the artificial tissue based high throughout screening. The invention can replace animal testing by the invention providing a physiological response system assembled from cultured cells.

In an aspect, the results of screening are employed to identify and advance one or more candidate pharmaceuticals or drugs to an advanced stage of further stage of testing or evaluation, including possibly commercialization. In another aspect, the results of screening are employed to terminate or alter further testing or screening on a pharmaceutical or drug candidate. In another aspect, the method and apparatus herein are used to evaluate and validate the target or locus for or of the drug or pharmaceutical candidate.

While the invention has been described in terms of various specific embodiments, those skilled in the art will recognize that the invention can be practiced with modification within the spirit and scope of the claims.

REFERENCES

1. Petersen, N. O., W. B. McConnaughey, and E. L. Elson. 1982. Dependence of locally measured cellular deformability on position on the cell, temperature, and cytochalasin B. *Proceedings of the National Academy of Sciences of the United States of America.* 79:5327-31.
2. Sundberg, S. A. 2000. High-throughput and ultra-high-throughput screening: solution- and cell-based approaches. *Curr Opin Biotechnol.* 11:47-53.
3. Zahalak, G. I., W. B. McConnaughey, and E. L. Elson. 1990. Determination of cellular mechanical properties by cell poking, with an application to leukocytes. *Journal of Biomechanical Engineering.* 112:283-94.

What is claimed is:

1. A method of measuring a tissue response comprising:
   a) forming and suspending a bio-artificial tissue on a scaffold to yield a bio-artificial tissue overlaying the scaffold without a fastener to facilitate tissue adhesion;
   b) contacting a bio-artificial tissue with a test agent;
   c) applying a mechanical force to the contacted bio-artificial tissue of step (b); and
   d) measuring a mechanical response of the contacted bio-artificial tissue on the scaffold to the test agent, the mechanical response being at least one of tissue stiffness and contractile force of the bio-artificial issue.

2. The method of claim 1, wherein the mechanical response comprises tissue stiffness and contractile force.

3. The method of claim 1, wherein measuring the tissue stiffness includes measuring at least one of hysteresis, phase lag and dynamic stiffness.

4. The method of claim 1, wherein the bio-artificial tissue comprises cells and collagen.

5. The method of claim 1, wherein the bio-artificial tissue comprises muscle cells.

6. The method of claim 1, wherein the bio-artificial tissue comprises non-muscle cells.

7. The method of claim 1, wherein the bio-artificial tissue comprises endothelial cells.

8. The method of claim 1, wherein the bio-artificial tissue comprises cardiac cells.

9. The method of claim 1, wherein the bio-artificial tissue comprises extracellular matrix.

10. The method of claim 1, wherein the bio-artificial tissue comprises muscle cells and non-muscle cells.

11. The method of claim 1, wherein the bio-artificial tissue is suspended from a scaffold positioned within a multi-well plate to provide an array of locations in which responses are measured.

12. The method of claim 1, wherein the mechanical response is measured using a tissue indentation system.

13. The method of claim 12, wherein the tissue indentation system comprises an indentation probe coupled to a force transducer and a computer.

14. The method of claim 1, wherein a plurality of bio-artificial tissues are contacted with varying concentrations of the test agent to generate a dose response profile of the bio-artificial tissue to the test agent.

15. The method of claim 1, further comprising comparing the mechanical response of the bio-artificial tissue to contact with the test agent to the mechanical response of the bio-artificial tissue to contact with a second test agent.

16. The method of claim 15, wherein the mechanical responses are ranked based on a comparison of the mechanical responses of the bio-artificial tissue to a plurality of test agents.

17. The method of claim 1, wherein the bio-artificial tissue comprises cells known to be involved in a disease.

18. The method of claim 1, further comprising correlating the mechanical response with a cell present in the bio-artificial tissue.

19. The method of claim 1, further comprising:
   e) applying a mechanical force to the bio-artificial tissue and measuring the mechanical response of the bio-artificial tissue prior to contact with the test agent in step (b); and f) comparing the mechanical response of the bio-artificial tissue contacted with the test agent to the mechanical response of the bio-artificial tissue prior to contact with the test agent.

20. A method for screening the effects of pharmaceutical agents comprising:
   a) forming and suspending a bio-artificial tissue on a scaffold to yield a bio-artificial tissue overlaying the scaffold without a fastener to facilitate tissue adhesion;
   b) contacting the bio-artificial tissue with a pharmaceutical agent;
   c) applying a mechanical force to the contacted bio-artificial tissue of step (b);
   d) measuring a parameter of tissue stiffness or contractile force of the bio-artificial tissue on the scaffold;
   e) repeating steps (a) through (d) with at least another pharmaceutical agent; and
   f) identifying pharmaceutical agents that alter the tissue stiffness or contractile force of the bio-artificial tissue as compared to the tissue stiffness or contractile force of a bio-artificial tissue that is not contacted with the pharmaceutical agent.

21. The method of claim 20, wherein the parameter comprises tissue stiffness and contractile force.

22. The method of claim 20, wherein the tissue stiffness includes at least one of hysteresis, phase lag and dynamic stiffness.

23. The method of claim 20, wherein the bio-artificial tissue comprises cells and collagen.

24. The method of claim 20, wherein the bio-artificial tissue comprises muscle cells.

25. The method of claim 20, wherein the bio-artificial tissue comprises non-muscle cells.

26. The method of claim 20, wherein the bio-artificial tissue comprises endothelial cells.

27. The method of claim 20, wherein the bio-artificial tissue comprises cardiac cells.

28. The method of claim 20, wherein the bio-artificial tissue comprises muscle cells and non-muscle cells.

29. The method of claim 20, wherein the bio-artificial tissue comprises extracellular matrix.

30. The method of claim 20, wherein the bio-artificial tissue is suspended from a scaffold positioned within a well in a multi-well plate to provide an array of locations in which responses are measured.

31. The method of claim 20, wherein the tissue stiffness is measured using a tissue indentation system.

32. The method of claim 31, wherein the tissue indentation system comprises an indentation probe coupled to a force transducer and a computer.

33. The method of claim 20, wherein a plurality of bio-artificial tissues are contacted with varying concentrations of the pharmaceutical agent to generate a dose response profile of the bio-artificial tissue to the pharmaceutical agent.

34. The method of claim 20, further comprising comparing the response of the bio-artificial tissue to contact with the pharmaceutical agent to the response of the bio-artificial tissue to contact with a second pharmaceutical agent.

35. The method of claim 34, wherein the pharmaceutical agents are ranked based on a comparison of the tissue stiffness or contractile force of the bio-artificial tissue to a plurality of pharmaceutical agents.

36. The method of claim 20, wherein the bio-artificial tissue comprises cells known to be involved in a disease.

37. The method of claim 20, further comprising correlating the tissue stiffness or contractile force with a cell present in the bio-artificial tissue.

38. The method of claim 20, further comprising:
   g) applying a mechanical force to the bio-artificial tissue and measuring the mechanical response of the bio-artificial tissue prior to contact with the pharmaceutical agent in step (b); and
   h) comparing the mechanical response of the bio-artificial tissue contacted with the pharmaceutical agent to the mechanical response of the bio-artificial tissue prior to contact with the pharmaceutical agent.

39. A tissue response system, comprising:
   a) a plurality of bio-artificial tissues suspended from and overlaying a plurality of scaffolds without a fastener to facilitate tissue adhesion to the scaffold; each of the plurality of scaffolds positioned within a well in a multi-well plate to provide an array of locations in which responses of the bio-artificial tissue on the scaffold to a test agent can be measured; and
   b) a tissue indentation system for applying a mechanical force and measuring a mechanical response of the bio-artificial tissue, the system comprising a probe coupled to a force transducer and a computer, the probe capable of contacting the bio-artificial tissue and measuring a response of the bio-artificial tissue to the test agent, the response being at least one of contractile force and tissue stiffness.

40. A tissue response system, comprising:
   a) a bio-artificial tissue formed on and overlaying a scaffold, the bio-artificial tissue suspended without a fastener to facilitate tissue adhesion to the scaffold;
   b) a well for holding the scaffold, wherein the suspended bio-artificial tissue can be contacted with a test agent; and
   c) a tissue indentation system for applying a mechanical force and measuring a mechanical response of the bio-artificial tissue, the system comprising an indentation probe coupled to a force transducer and a computer, the probe capable of contacting the bio-artificial tissue on the scaffold and measuring a response of the bio-artificial tissue to the test agent, the response being at least one of contractile force and tissue stiffness.

41. The system of claim 40, wherein the response comprises tissue stiffness and contractile force.

42. The system of claim 40, wherein tissue stiffness includes at least one of hysteresis, phase lag and dynamic stiffness.

43. The system of claim 40, wherein the bio-artificial tissue comprises cells and collagen.

44. The system of claim 40, wherein the bio-artificial tissue comprises muscle cells.

45. The system of claim 40, wherein the bio-artificial tissue comprises non-muscle cells.

46. The system of claim 40, wherein the bio-artificial tissue comprises endothelial cells.

47. The system of claim 40, wherein the bio-artificial tissue comprises cardiac cells.

48. The system of claim 40, wherein the bio-artificial tissue comprises muscle cells and non-muscle cells.

49. The system of claim 40, wherein the bio-artificial tissue comprises extracellular matrix.

50. The system of claim 40, wherein the scaffold is positioned within a well in a multi-well plate to provide an array of locations in which responses are measured.

51. The system of claim 40, wherein a plurality of bio-artificial tissues suspended from a plurality of scaffolds is contacted with varying concentrations of the test agent, and the measured response is used to generate a dose response profile of the bio-artificial tissue to the test agent.

52. The system of claim 40, wherein the response of the bio-artificial tissue to contact with the test agent is compared to the response of the bio-artificial tissue to contact with a second test agent.

53. The system of claim 52, wherein the test agents are ranked based on a comparison of the tissue stiffness or contractile force of the bio-artificial tissue to a plurality of agents.

54. The system of claim 40, wherein the bio-artificial tissue comprises cells known to be involved in a disease.

55. The system of claim 40, wherein the response is associated with a cell present in the bio-artificial tissue.

56. A method of measuring a tissue response comprising:
   a) forming and suspending a bio-artificial tissue on a scaffold to yield a bio-artificial tissue overlaying the scaffold without a fastener to facilitate tissue adhesion;
   b) contacting the bio-artificial tissue with an agent known to alter a mechanical response of a tissue;
   c) contacting the bio-artificial tissue of step (b) with a test agent;
   d) applying a mechanical force to the contacted bio-artificial tissue of step (c);
   e) measuring a mechanical response of the contacted bio-artificial tissue on the scaffold, the mechanical response being at least one of contractile force and tissue stiffness of the bio-artificial tissue; and
   f) comparing the mechanical response of the bio-artificial tissue contacted with both the agent known to alter a mechanical response of a tissue and the test agent to the mechanical response of at least one of (1) the bio-artificial tissue prior to contact with any agent; (2) a bio-artificial tissue only contacted with an agent known to alter the mechanical response of a tissue; or (3) a bio-artificial tissue only contacted with the test agent.

57. The method of claim 56, wherein the bio-artificial tissue is contacted with the test agent prior to being contacted with the agent known to alter a mechanical response.

58. The method of claim 56, wherein the bio-artificial tissue is contacted with the test agent at the same time as being contacted with the agent known to alter a mechanical response.

59. The method of claim 56, wherein the bio-artificial tissue is contacted with the test agent after being contacted with the agent known to alter a mechanical response.

60. The method of claim 56, wherein the mechanical response comprises tissue stiffness and contractile force.

61. The method of claim 56, wherein the tissue stiffness includes at least one of hysteresis, phase lag and dynamic stiffness.

62. The method of claim 56, wherein the bio-artificial tissue comprises cells and collagen.

63. The method of claim 56, wherein the bio-artificial tissue comprises muscle cells.

64. The method of claim 56, wherein the bio-artificial tissue comprises non-muscle cells.

65. The method of claim 56, wherein the bio-artificial tissue comprises endothelial cells.

66. The method of claim 56, wherein the bio-artificial tissue comprises cardiac cells.

67. The method of claim 56, wherein the bio-artificial tissue comprises muscle cells and non-muscle cells.

68. The method of claim 56, wherein the bio-artificial tissue comprises extracellular matrix.

69. The method of claim 56, wherein the bio-artificial tissue is suspended from a scaffold positioned within a well in a multi-well plate to provide an array of locations in which responses are measured.

70. The method of claim 56, wherein the tissue stiffness is measured using a tissue indentation system.

71. The method of claim 70, wherein the tissue indentation system comprises an indentation probe coupled to a force transducer and a computer.

72. A method of measuring a tissue response comprising:
   a) positioning a scaffold within a well in a multi-well plate;
   b) forming and suspending a bio-artificial tissue on the scaffold to yield a bio-artificial tissue overlaying the scaffold without a fastener to facilitate tissue adhesion;
   c) contacting the bio-artificial tissue with a test agent;
   d) applying a mechanical force to the contacted bio-artificial tissue of step (c); and
   e) measuring a mechanical response of the contacted bio-artificial tissue on the scaffold to the test agent, the mechanical response being at least one of tissue stiffness and contractile force and comparing the mechanical response to a mechanical response of a bio-artificial tissue that is not contacted with the test agent.

73. A method of measuring a tissue response comprising:
   a) forming and suspending a bio-artificial tissue on a scaffold to yield a bio-artificial tissue overlaying the scaffold without a fastener to facilitate tissue adhesion;
   b) contacting the bio-artificial tissue with a test agent;
   c) applying a mechanical force to the contacted bio-artificial tissue of step (b) using a tissue indentation system; and
   d) measuring a mechanical response of the contacted bio-artificial tissue on the scaffold to the test agent using the tissue indentation system, the mechanical response being at least one of tissue stiffness and contractile force and comparing the mechanical response to a mechanical response of a bio-artificial tissue that is not contacted with the test agent.

74. The method of claim 73, wherein the tissue indentation system comprises an indentation probe coupled to a force transducer and a computer.

75. A method for screening the effects of pharmaceutical agents comprising:
   a) forming and suspending a bio-artificial tissue on a scaffold to yield a bio-artificial tissue overlaying the scaffold without a fastener to facilitate tissue adhesion;
   b) contacting the bio-artificial tissue with a pharmaceutical agent;
   c) applying a mechanical force to the contacted bio-artificial tissue of step (b) using a tissue indentation system;
   d) measuring a parameter of tissue stiffness or contractile force of the bio-artificial tissue on the scaffold to the pharmaceutical agent using the tissue indentation system;
   e) repeating steps (a) through (d) with at least another pharmaceutical agent; and
   f) identifying pharmaceutical agents that alter the tissue stiffness or contractile force of the contacted bio-artificial tissue as compared to the tissue stiffness or contractile force of a bio-artificial tissue that is not contacted with the pharmaceutical agent.

76. The method of claim 75, wherein the tissue indentation system comprises an indentation probe coupled to a force transducer and a computer.

77. A method of measuring a tissue response comprising:
   a) positioning a scaffold within a well in a multi-well plate;
   b) forming and suspending a bio-artificial tissue on the scaffold to yield a bio-artificial tissue overlaying the scaffold without a fastener to facilitate tissue adhesion;

c) contacting the bio-artificial tissue with an agent known to alter a mechanical response of a tissue;
d) applying a mechanical force to the contacted bio-artificial tissue of step (c);
e) measuring a mechanical response of the contacted bio-artificial tissue on the scaffold, the mechanical response being at least one of contractile force and tissue stiffness of the bio-artificial tissue;
f) contacting the bio-artificial tissue of step (e) with a test agent;
g) applying a mechanical force to the contacted bio-artificial tissue of step (f);
h) measuring a mechanical response of the contacted bio-artificial tissue of step (f) on the scaffold, the mechanical response being at least one of contractile force and tissue stiffness of the bio-artificial tissue; and
i) comparing the response of the bio-artificial tissue contacted with the agent known to alter a mechanical response from step (e) to the response of the bio-artificial tissue further contacted with the test agent from step (h).

78. A method of measuring a tissue response comprising:
a) forming and suspending a bio-artificial tissue on a scaffold to yield a bio-artificial tissue overlaying the scaffold without a fastener to facilitate tissue adhesion;
b) contacting the bio-artificial tissue with an agent known to alter a mechanical response;
c) contacting the bio-artificial tissue with a test agent;
d) applying a mechanical force to the contacted bio-artificial tissue of step (c);
e) measuring tissue stiffness of the bio-artificial tissue of step (d) using a tissue indentation system, wherein said bio-artificial tissue remains suspended without a fastener to facilitate tissue adhesion from said scaffold; and
f) comparing the tissue stiffness of a bio-artificial tissue contacted with the agent known to alter a mechanical response to the tissue stiffness of the bio-artificial tissue contacted with both the agent known to alter a mechanical response and the test agent.

79. The method of claim 78, wherein the tissue indentation system comprises an indentation probe coupled to a force transducer and a computer.

* * * * *

UNITED STATES PATENT AND TRADEMARK OFFICE
CERTIFICATE OF CORRECTION

| | | |
|---|---|---|
| PATENT NO. | : 7,449,306 B2 | Page 1 of 1 |
| APPLICATION NO. | : 10/219097 | |
| DATED | : November 11, 2008 | |
| INVENTOR(S) | : Elliot Elson, William B. McConnaughey and Tetsuro Wakatsuki | |

It is certified that error appears in the above-identified patent and that said Letters Patent is hereby corrected as shown below:

Column 1, line 10, please insert the following paragraph:

--STATEMENT REGARDING FEDERALLY SPONSORED RESEARCH

This invention was made with government support under RO1 GM038838 awarded by the National Institutes of Health. The government has certain rights in the invention.--

Signed and Sealed this
Twentieth Day of September, 2011

David J. Kappos
*Director of the United States Patent and Trademark Office*